(12) United States Patent
Perthu

(10) Patent No.: US 11,224,698 B2
(45) Date of Patent: Jan. 18, 2022

(54) INJECTION DEVICE

(71) Applicant: UNION MEDICO ApS, Copenhagen (DK)

(72) Inventor: Michael Perthu, Copenhagen (DK)

(73) Assignee: UNION MEDICO APS, Copenhagen N (DK)

( * ) Notice: Subject to any disclaimer, the term of this patent is extended or adjusted under 35 U.S.C. 154(b) by 217 days.

(21) Appl. No.: 16/437,428

(22) Filed: Jun. 11, 2019

(65) Prior Publication Data

US 2019/0307968 A1   Oct. 10, 2019

Related U.S. Application Data

(63) Continuation-in-part of application No. 16/217,572, filed on Dec. 12, 2018, now abandoned, which is a continuation of application No. 14/909,507, filed as application No. PCT/DK2014/000040 on Jul. 30, 2014, now abandoned.

(30) Foreign Application Priority Data

Aug. 2, 2013 (DK) .............................. PA201370426
Aug. 2, 2013 (DK) .............................. PA201370427

(51) Int. Cl.
*A61M 5/32* (2006.01)
*A61M 5/20* (2006.01)

(52) U.S. Cl.
CPC ........ *A61M 5/3204* (2013.01); *A61M 5/3202* (2013.01); *A61M 5/3287* (2013.01); *A61M 5/3243* (2013.01); *A61M 2005/202* (2013.01); *A61M 2005/208* (2013.01); *A61M 2005/2073* (2013.01); *A61M 2205/13* (2013.01); *A61M 2205/43* (2013.01); *A61M 2205/581* (2013.01); *A61M 2205/583* (2013.01); *A61M 2205/586* (2013.01)

(58) Field of Classification Search
CPC .............. A61M 5/3204; A61M 5/3202; A61M 5/3287; A61M 5/3243; A61M 2005/206; A61M 5/46; A61M 2005/202; A61M 2005/2073; A61M 2005/208; A61M 2205/13; A61M 2205/43; A61M 2205/581; A61M 2205/583; A61M 2205/586
See application file for complete search history.

(56) References Cited

U.S. PATENT DOCUMENTS

| 1,320,536 | A | * | 11/1919 | Di Falco | ............. | A61M 5/3287 604/157 |
| 2,047,010 | A | * | 7/1936 | Dickinson | ........... | A61M 5/3287 604/157 |
| 6,595,962 | B1 | * | 7/2003 | Perthu | ................. | A61M 5/3287 604/157 |

\* cited by examiner

*Primary Examiner* — Brandy S Lee
*Assistant Examiner* — Hong-Van N Trinh
(74) *Attorney, Agent, or Firm* — Maier & Maier, PLLC

(57) ABSTRACT

Disclosed is an injection device for injecting a hypodermic syringe along an injection direction defining an injection axis. The injection device comprises a housing for being positioned at a user's skin, and a movable element movably arranged relative to the housing between a retracted position and an injection position.

15 Claims, 18 Drawing Sheets

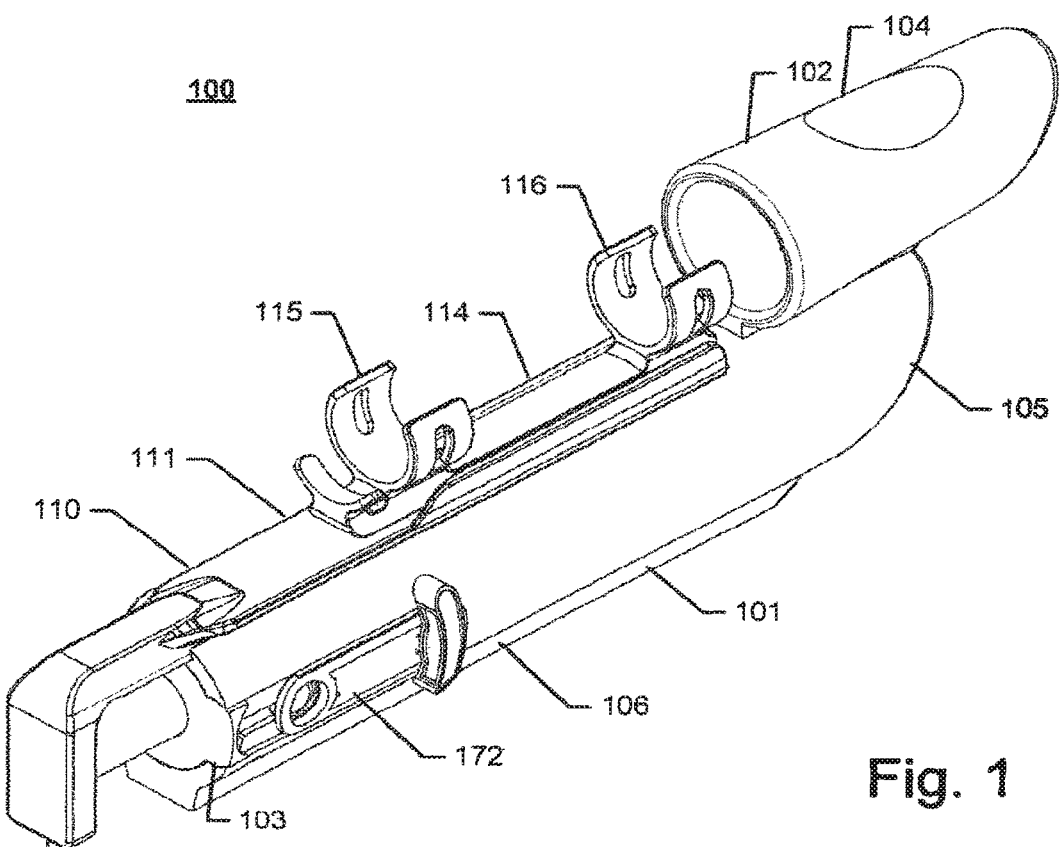
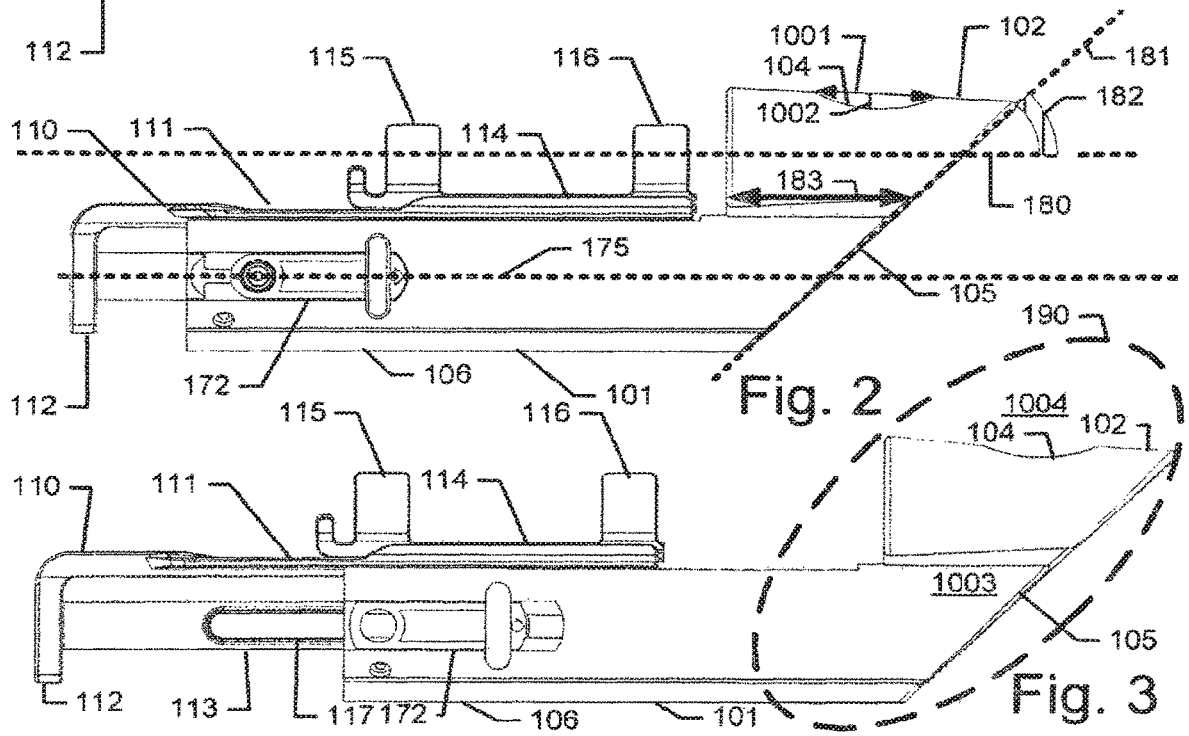

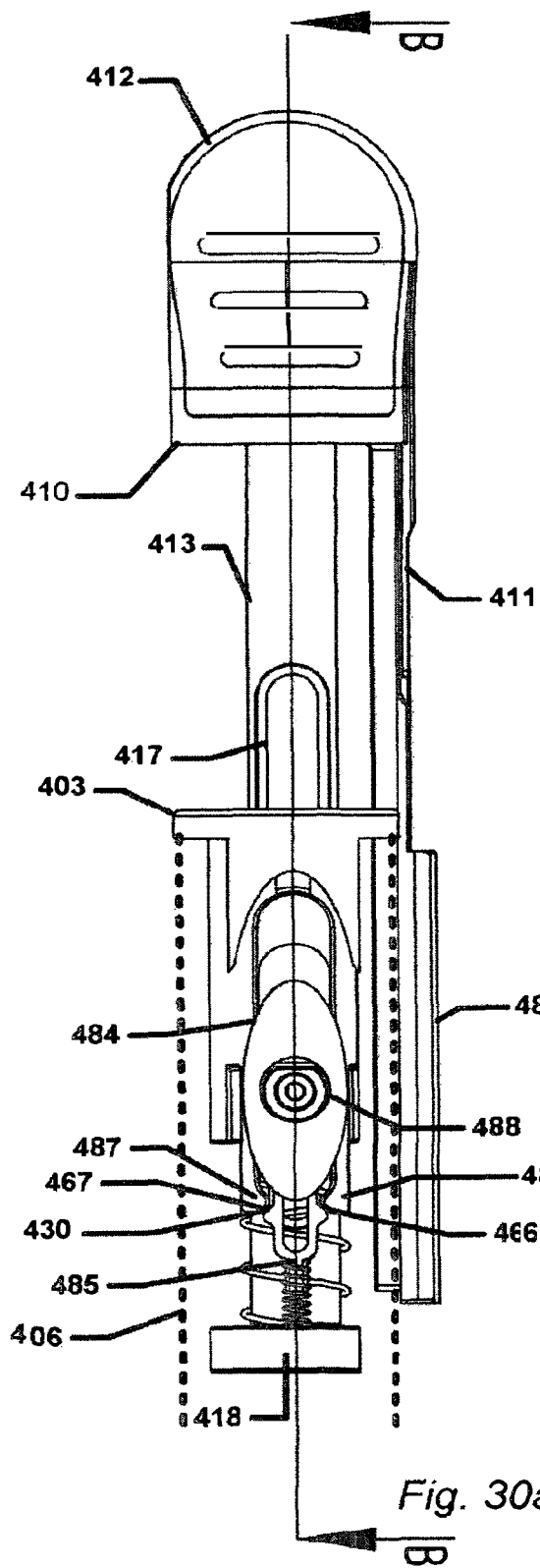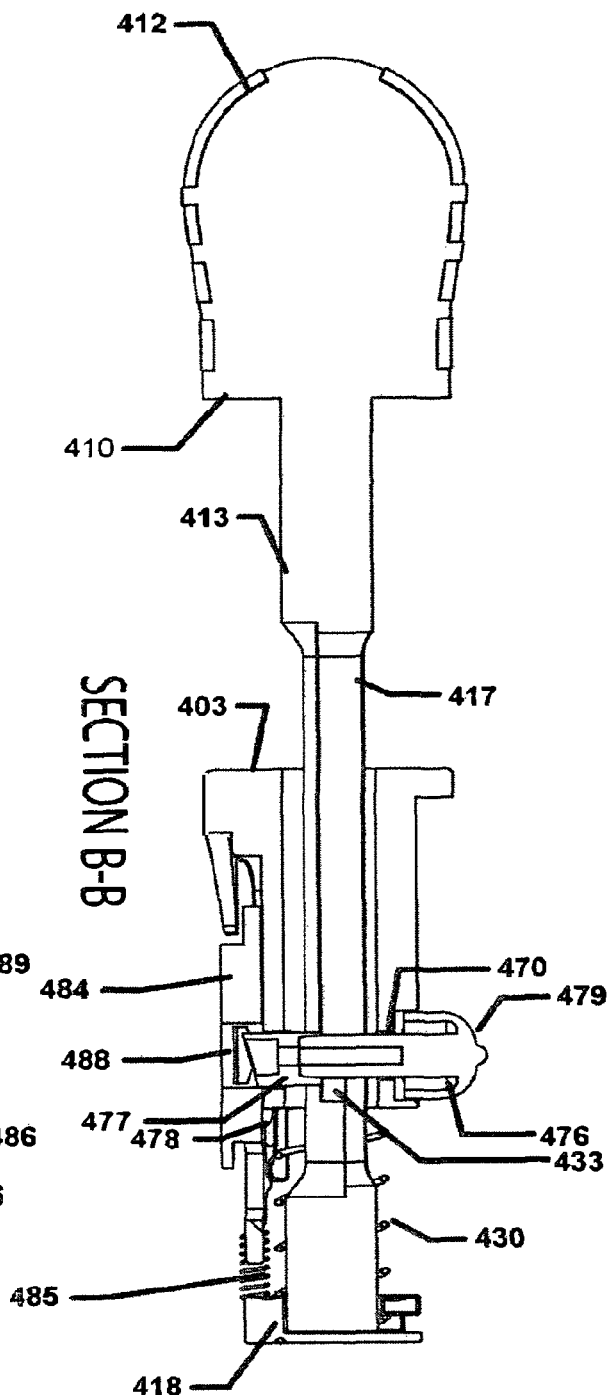
Fig. 30a
Fig. 30b

INJECTION DEVICE

FIELD

The present invention relates to an automatic injector device. More specifically the invention relates to an automatic injector device for injection of a syringe.

BACKGROUND

Many people in their daily lives are faced with the task of injecting hypodermic syringes. The purpose of these injections may both be for therapeutic treatment, prophylactic treatment or cosmetic treatment. Examples of therapeutic treatment are subcutaneous delivery of insulin for diabetics, subcutaneous delivery of epinephrine for people suffering from Anaphylaxis, intramuscular and/or subcutaneous delivery of antibiotics for treating infections, and intramuscular delivery of drugs for treatment of Multiple Sclerosis. Examples of prophylactic treatment are intramuscular delivery of vitamins, subcutaneous delivery of vaccines, and intramuscular and/or subcutaneous delivery of medicaments.

The injections may be performed by the users themselves or by medical professionals. In both cases it is desirable to secure that the injections are performed in a safe and controlled manner. This may be achieved by using an automatic injecting device configured to automatically inject a syringe.

U.S. Pat. No. 2,295,849 discloses a device for injecting a hypodermic syringe comprising a stationary part for being placed against the skin of a recipient and a movable part for holding a syringe, wherein the movable part is connected to the stationary part through a spring. The automatic injector is configured to automatically inject a syringe and further automatically deliver the content of the syringe to the patient.

AU8704582 discloses a device for injecting a hypodermic syringe in a 20 degree angle relative to the skin of the recipient. The device comprises a wedge shaped stationary part for being placed against the skin of a recipient and a movable part for holding a syringe.

EP1154811 discloses an injection device comprising a slide which can be displaced in relation to a housing from a retracted position to an injection position, and which comprises a portion situated within the housing and a portion situated outside the housing, both portions being interconnected through a groove in the housing.

U.S. Pat. No. 3,941,130A discloses an injection device for a hypodermic syringe including structure for supporting a syringe and projecting the needle of the syringe into a skin tissue area against which a predetermined portion of the injection device has been placed. Also structure is provided for slightly retracting the plunger of the syringe relative to the barrel portion thereof during the projection of the needle of the syringe into the adjacent skin tissue area and further structure is provided for shifting the piston portion of the syringe, relative to the barrel portion thereof, in order to express the liquid contents of the syringe through the needle thereof after the needle has been projected in order to force the needle carried by the barrel portion of the syringe into the adjacent skin tissue However, it remains a problem to:
provide a device for automatically injecting hypodermic syringes than can be operated easily and safely;
provide a more structural stable device for automatically injecting hypodermic syringes that can be manufactured in inexpensive materials such as plastics;
provide a device for automatically injecting hypodermic syringes that can be better controlled during the injection process.

SUMMARY

According to a first aspect, the invention relates to an injection device for injecting a hypodermic syringe along an injection direction defining an injection axis, wherein said injecting device comprises:
  a housing for being positioned at a user's skin, wherein said housing comprises a first tubular element having an upper opening; and
  a movable element movably arranged relative to said housing between a retracted position and an injection position, wherein said movable element comprises a hypodermic syringe holder for holding a hypodermic syringe
wherein said movable element comprises a first portion arranged to slide inside said first tubular element of said housing, a second portion arranged to slide at a first outer surface of said housing, and a connection portion connecting said first portion with said second portion, wherein said movable element extends out of said upper opening of said first tubular element.

Consequently, a more a structural stable injection device is provided as the first tubular element may be formed without a slit. This allows the injection device to be created in inexpensive materials such as plastics.

The structural stability is further improved since both the first portion and the second portion of the movable element can slide on different parts of the housing.

The housing and/or the movable element may be made of plastic. The end of the first tubular element facing the skin of the user may be closed. Thus in use, the upper opening of the first tubular element faces away from the skin of the user. The second part of the movable element may slide at a first outer surface of the first tubular element or another element of the housing e.g. an element attached to the first tubular element. The housing and the movable element may be practically non-deformable during normal use i.e. the housing and the movable element may deform less than 5% during normal use. The movable element may have a u-shape, wherein the first portion is the first leg of the U and the second portion is the second leg of the U and the connection portion is the bottom part of the U. The first portion and the second portion of the movable element may have an approximately equal length or they may differ in length. The tubular element may have a round or rectangular cross-section. The syringe holder may be connected to the second portion of the movable element. The syringe holder may comprise a first set of gripping arms and a second set of gripping arms. The syringe holder may be detachably connected to the movable element, whereby it can be exchanged allowing the same injection device to be used together with different sized hypodermic syringes. The injection device may comprise a release mechanism for initiating an injection of a hypodermic syringe. The release mechanism may be a release mechanism as explained in relation to the seventh aspect of the invention. The injection device may be configured so that when said movable element is in said retracted position and said release mechanism is pushed said movable element moves to said injection position whereby a hypodermic syringe attached to said hypodermic syringe holder may be injected.

In some embodiments, said movable element is arranged in a manner relative to said housing so that at least 50% of the outer circumference of any cross-section of said housing being perpendicular to said injection axis does not interact with said movable element at any possible position of said movable element.

In some embodiments, said movable element is arranged in a manner relative to said housing so that at least 65% of the outer circumference of any cross-section of said housing being perpendicular to said injection axis does not interact with said movable element at any possible position of said movable element.

This allows the user to more freely grip and handle the injection device e.g. a gripping zone may be formed in the lower third part of the injection device providing better control to the user.

In some embodiments, said housing further comprises a needle shield.

The needle shield may be arranged so that the tip of a hypodermic needle of a hypodermic syringe attached to said hypodermic syringe is positioned inside the needle shield when the movable element is in the retracted position. The needle shield may be a tubular needle shield. The tubular needle shield comprises a first opening facing a user's skin when the injection device is positioned at the skin of the user. The housing may comprise a planar contact surface for being positioned at a user's skin, wherein the first opening forms part of said planar contact surface.

By having a needle shield the user may be protected from being stung by a hypodermic needle. This is especially important when the injection device is used by professional medical personnel, as it reduces the risk that the professional medical personnel is infected with diseases such as HIV or Hepatitis from the patients they are helping.

In some embodiments, said housing comprises a gripping zone, said needle shield forms part of said gripping zone and wherein said gripping zone is configured to allow a user to safely hold said injection device at any position of said gripping zone while a hypodermic syringe is being injected.

In some embodiments, said injection device is configured so that when said movable element is in said retracted position said first portion is extending out of said first tubular element through said upper opening of said first tubular element, and when said movable element is in said injection position said first portion is entirely positioned inside said first tubular element and said second portion and said connection portion is positioned entirely outside said housing.

In some embodiments, said first outer surface of said housing comprises a guide extending along said injection axis, and said second portion of said movable element engages with said guide, and wherein in said guide prevents said second portion of said movable element from moving in any other direction than along said injection axis.

Consequently, the structural strength of the injection device may be further improved.

In some embodiments, said guide is a groove extending along said injection axis, wherein said groove is configured to grip said second portion of said movable element, whereby said second portion of said movable element is prevented from moving in any other direction than along said injection axis.

The groove may comprise a first wall and a second wall that slope inwards, whereby said second portion is prevented from moving in any other direction than along said injection axis. The entire second portion of the movable element may slide inside the groove or only a part of said second portion may slide inside said groove.

In some embodiments, said connection portion comprises a handle allowing a user, when said movable element is in said injection position, to grip said movable element and retract said movable element back into said retracted position.

In some embodiments, said handle comprises a first gripping zone.

The first handle gripping zone may comprise a material configured to establish a high frictional grip with the hand of a user.

In some embodiments, the handle comprises a first protruding gripping portion protruding in a direction being perpendicular to the injection axis.

In some embodiments, the handle comprises a second protruding gripping portion protruding in a direction being perpendicular to the injection axis, and said first protruding gripping portion.

In some embodiments, the handle comprises a second protruding gripping portion and a third protruding gripping portion both the second and third protruding gripping portion protruding in a direction being perpendicular to the injection axis, and said first protruding gripping portion.

Consequently, a user may more easily from any direction grip said handle.

In some embodiments, said injection device further comprises a spring connecting said movable element with said housing, wherein said spring, when released, is configured to move said movable element from said retracted position to said injection position.

The spring may be any kind of spring such as a mechanical spring or a gas spring. The spring may be a compression spring or an expansion spring.

In some embodiments, said first portion of said movable element comprises a disc having an outer surface interacting with said spring.

The disc may form the distal end of the first portion of the movable element. The disc may have any shape such as circular or rectangular.

The spring may be a compression spring, i.e. a spring that when compressed stores mechanical energy. The compression spring may surround a part of the first portion of the movable element, and have a first end that abuts a first upper surface of said disc. The upper surface of said disc is the surface that faces away from the user when the injection device is positioned at the skin of the user. Thus, when the movable element is in the retracted position, the compression spring is compressed and thereby stores mechanical energy that can be used to move said movable element from said retracted position to said injection position whereby a hypodermic syringe attached to said hypodermic syringe holder may be injected.

In some embodiments, said disc is configured to slide along an inner surface of said first tubular element thereby providing additional mechanical stability.

The disc may have a shape matching the shape of the inner surface of said first tubular element.

In some embodiments, said housing further comprises a second tubular element inserted into the top of said first tubular element, and wherein said movable element extends out of said second tubular element.

The second tubular element may be permanently attached to the first tubular element. The second tubular element may be attached using an adhesive and/or a press fit i.e. a frictional fit.

In some embodiments, said movable element is configured so that a part of said first portion slides along an inner surface of said second tubular element thereby providing additional mechanical stability.

Thus the first portion of the movable element may comprise an elongated part that slides along an inner surface of said second tubular element, and a disc that slides along an inners surface of first tubular element, wherein the largest width (measured in planes being perpendicular to the injection axis) of the elongated portion is lower than the largest width of the disc.

The spring may be a compression spring i.e. a spring that when compressed stores mechanical energy.

In some embodiments, the spring is a compression spring that surrounds a part of the first portion of the movable element, and has a first end that abuts a first upper surface of said disc, and a second end that abuts a lower surface of the second tubular element.

The upper surface of said disc is the surface that faces away from the skin of the user when the injection device is positioned at the skin of the user and the lower surface of the second tubular element is a surface that faces towards the skin of the user when the injection device is positioned at the skin of the user.

In some embodiments, said injection device is an intramuscular injection device for intramuscularly injecting a hypodermic syringe.

In some embodiments, said injection device is a subcutaneous injection device for subcutaneously injecting a hypodermic syringe along a central axis of said injection device.

In some embodiments, said housing comprises a planar contact surface for being positioned at the skin, wherein said planar contact surface is positioned in a plane being angled with an angle below 90 degrees relative to said injection axis.

Consequently, the injection device may be used for precise angled injections.

The angle between the planar contact surface and the injection axis is defined as the smaller of the two possible angels measurable between a plane and a line.

In some embodiments, said housing comprises a planar contact surface for being positioned at the skin, wherein said planar contact surface is positioned in a plane being angled with an angle below 80 degrees relative to said injection axis.

In some embodiments, said housing comprises a planar contact surface for being positioned at the skin, wherein said planar contact surface is positioned in a plane being angled with an angle below 75 degrees relative to said injection axis.

In some embodiments, said contact surface comprises a plurality of protrusions for establishing a high frictional contact with the skin.

According to a second aspect the invention relates to an injection device for injecting a hypodermic syringe along an injection direction defining an injection axis, wherein said injecting device comprises:
  a housing for being positioned at the skin, wherein said housing comprises an elongated main body and a needle shield attached to said elongated main body; and
  a movable element movably arranged relative to said housing between a retracted position and an injection position, wherein said movable element comprises a hypodermic syringe holder for holding a hypodermic syringe and a portion of the movable element is arranged to slide at a first outer surface of said housing;

wherein said housing comprises a gripping zone, said needle shield forms part of said gripping zone and wherein said gripping zone is configured to allow a user to safely hold said injection device at any position of said gripping zone while a hypodermic syringe is being injected by said injection device.

Consequently, the injection device may, in a safe manner, be gripped close to the skin of the user being injected. This provides better control, especially when the injection device is used for angled injections. By having a needle shield, the user may be protected from being stung by a hypodermic needle. This is especially important when the injection device is used by professional medical personnel, as it reduces the risk that the professional medical personnel is infected with diseases such as HIV or Hepatitis from the patients they are helping.

The housing and/or the movable element may be made of plastic. The gripping zone may be positioned in the lower third part of the housing. The lower third part of the housing is defined as the third part of the housing being closest to a user's skin when the injection device is positioned at a user's skin. The housing and the movable element may be practically non-deformable during normal use i.e. the housing and the movable element may deform less than 5% during normal use. The syringe holder may comprise a first set of gripping arms and a second set of gripping arms. The syringe holder may be detachably connected to the movable element, whereby it can be exchanged allowing the same injection device to be used together with different sized hypodermic syringes. The injection device may comprise a release mechanism for initiating an injection of a hypodermic syringe. The release mechanism may be a release mechanism as explained in relation to the seventh aspect of the invention. The injection device may be configured so that when said movable element is in said retracted position and said release mechanism is pushed, said movable element moves to said injection position whereby a hypodermic syringe attached to said hypodermic syringe holder may be injected. The needle shield may be a tubular needle shield. The needle shield may comprise a first opening facing a user's skin when the injection device is positioned at the skin of the user. The housing may comprise a planar contact surface for being positioned at a user's skin, wherein the first opening forms part of said planar contact surface.

In some embodiments, the needle shield is arranged so that the tip of a hypodermic needle of a hypodermic syringe attached to said hypodermic syringe holder is positioned completely inside the needle shield when the movable element is in the retracted position, and wherein said movable element can be retracted from the injection position to the retracted position.

Consequently, a medical professional may be protected from being stung both before and after an injection.

In some embodiments, the elongated main body is a first tubular element having an upper opening, and said movable element comprises a first portion arranged to slide inside said first tubular element of said housing, a second portion arranged to slide at a first outer surface of said housing, and a connection portion connecting said first portion with said second portion, wherein said movable element extends out of said upper opening of said first tubular element.

The end of the first tubular element facing the skin of the user may be closed. Thus in use the first tubular element faces away from the skin of the user. The second part of the movable element may slide at a first outer surface of the first tubular element or another element of the housing e.g. an element attached to the first tubular element. The movable element may have a u-shape, wherein the first portion is the first leg of the U and the second portion is the second leg of the U and the connection portion is the bottom part of the U. The first portion and the second portion of the movable element may have an approximately equal length or they may differ in length.

Alternatively, the first tubular element may comprise a longitudinal slot wherein a first portion of the movable element is arranged to slide inside said first tubular element of said housing, a second portion arranged to slide at a first outer surface of said housing, and a connection portion connecting said first portion with said second portion is extending through said longitudinal slot, The first tubular element may have a round or rectangular cross-section. The syringe holder may be connected to the second portion of the movable element. The syringe holder may comprise a first set of gripping arms and a second set of gripping arms. The syringe holder may be detachably connected to the movable element, whereby it can be exchanged allowing the same injection device to be used together with different sized hypodermic syringes. The injection device may comprise a release mechanism for initiating an injection of a hypodermic syringe. The release mechanism may be a release mechanism as explained in relation to the seventh aspect of the invention. The injection device may be configured so that when said movable element is in said retracted position and said release mechanism is pushed said movable element moves to said injection position whereby a hypodermic syringe attached to said hypodermic syringe holder may be injected.

In some embodiments, said movable element is arranged in a manner relative to said housing so that at least 50% of the outer circumference of any cross-section of said housing being perpendicular to said injection axis does not interact with said movable element at any possible position of said movable element.

In some embodiments, said movable element is arranged in a manner relative to said housing so that at least 65% of the outer circumference of any cross-section of said housing being perpendicular to said injection axis does not interact with said movable element at any possible position of said movable element.

Consequently a user may grip said injection device from behind at said gripping zone without risking interfering with the movement of said movable element.

This allows a user to safely grip said injection device at positions closer to the skin of the user.

In some embodiments, said needle shield has a minimum height of at least 1 cm.

In some embodiments, said needle shield has a minimum height of at least 1.5 cm.

In some embodiments, said needle shield has a minimum height of at least 2 cm.

The minimum height is measured as the minimum width of the needle shield along the injection axis.

In some embodiments, said gripping zone comprises a first concave portion for receiving one or more fingers.

In some embodiments, said gripping zone further comprises a second concave portion for receiving one or more fingers.

In some embodiments, said first concave portion and/or said second concave portion comprises a plurality of protruding elements for providing a high frictional contact with the fingers of a user.

In some embodiments, a part of said gripping zone comprises a material for establishing a high frictional contact with the hand of a user.

The material may be a rubber or rubber like material.

In some embodiments, said needle shield is an assembly assembled from a first part attached to said elongated main body, and a second part inserted into said first part.

In some embodiments, said needle shield and said elongated main body is integrally formed.

In some embodiments, said needle shield and said elongated main body is integrally moulded.

In some embodiments, said injection device is an intramuscular injection device for intramuscularly injecting a hypodermic syringe.

In some embodiments, said injection device is a subcutaneous injection device for subcutaneously injecting a hypodermic syringe along a central axis of said injection device.

In some embodiments, said housing comprises a planar contact surface for being positioned at the skin, wherein said planar contact surface is positioned in a plane being angled with an angle below 90 degrees relative to said injection axis.

Consequently, the injection device may be used for precise angled injections.

The angle between the planar contact surface and the injection axis is defined as the smaller of the two possible angels measurable between a plan and a line.

In some embodiments, said housing comprises a planar contact surface for being positioned at the skin, wherein said planar contact surface is positioned in a plane being angled with an angle below 80 degrees relative to said injection axis.

In some embodiments, said housing comprises a planar contact surface for being positioned at the skin, wherein said planar contact surface is positioned in a plane being angled with an angle below 75 degrees relative to said injection axis.

In some embodiments, said contact surface comprises a plurality of protrusions for establishing a high frictional contact with the skin.

In some embodiments, said needle shield comprises an inspection window arranged at a position allowing a user to inspect said hypodermic needle or needle hub.

Consequently, said needle shield may be fitted with gripping features limiting the transparency of the needle shield without preventing the user from inspecting an injection, e.g. from securing that a blood vessel has not been hit.

For a large number of treatments, it is important to secure that the active substance is deposited subcutaneously or intramuscularly, and not delivered directly into a blood vessel since the effect then may be very short. Thus after a hypodermic syringe has been injected using an injector device, the user typically withdraw the plunger a small amount and watches the syringe for blood. If no blood is withdrawn into the syringe, the user knows that a suitable injection position has been chosen and may continue with injecting the active substance of the syringe by pushing the plunger.

It may however be difficult for the user to detect a small amount of blood withdrawn into the syringe.

Thus, it remains a problem to provide a device allowing the user to more easily detect whether the chosen injection position is suitable.

According to a third aspect, the invention relates to an injection device for injecting a hypodermic syringe along an injection direction, said injection direction defining an injection axis, wherein said injecting device comprises:

a housing for being positioned at a user's skin, wherein said housing comprises an elongated main body, a needle shield attached to said elongated main body, and a light source; and a movable element movably arranged relative to said housing between a retracted position and an injection position, wherein said movable element comprises a hypodermic syringe holder for holding a hypodermic syringe connected to a hypodermic needle through a needle hub;

wherein said light source is arranged so that when it is activated and the movable element is in the injection position, the peak intensity of the resulting light beam is positioned at or below said needle hub thereby allowing a user to detect blood present in the needle hub or in the hypodermic needle.

Consequently, if the hypodermic needle is injected into a blood vessel, blood may be detected in the needle hub or in the hypodermic needle before the content of hypodermic syringe is contaminated. This allows the user to withdraw the injection device, and change the needle hub and the hypodermic needle without having to discard the medicine stored in hypodermic syringe.

The housing and/or the movable element may be made of plastic. The housing and the movable element may be practically non-deformable during normal use i.e. the housing and the movable element may deform less than 5% during normal use. The syringe holder may be detachably connected to the movable element, whereby it can be exchanged allowing the same injection device to be used together with different sized hypodermic syringes. The injection device may comprise a release mechanism for initiating an injection of a hypodermic syringe. The release mechanism may be a release mechanism as explained in relation to the seventh aspect of the invention. The injection device may be configured so that when said movable element is in said retracted position and said release mechanism is pushed said movable element moves to said injection position whereby a hypodermic syringe attached to said hypodermic syringe holder may be injected.

In some embodiments, said syringe holder comprises groove for gripping a collar of said hypodermic syringe wherein said groove is configured to prevent said hypodermic syringe to move relative to said hypodermic syringe holder along said injection axis.

In some embodiments, said light source is arranged so that when it is activated and the movable element is in the injection position, the peak intensity of the resulting light beam is positioned at said needle hub thereby allowing a user to detect blood present in the needle hub.

In some embodiments, said housing comprises a planar contact surface for being positioned at the skin, wherein said light source is arranged with a distance to said planar contact surface between 0 cm and 2 cm, 0 cm and 1.5 cm, or 0 cm and 1 cm.

In some embodiments, said needle shield is arranged so that the tip of a hypodermic needle of a hypodermic syringe attached to said hypodermic syringe holder is positioned completely inside the needle shield when the movable element is in the retracted position, and wherein said movable element can be retracted from the injection position to the retracted position.

The needle shield may comprise a first opening facing a user's skin when the injection device is positioned at the skin of the user. The housing may comprise a planar contact surface for being positioned at a user's skin, wherein the first opening forms part of said planar contact surface. The light source may be positioned inside said needle shield.

In some embodiments, said needle shield comprises an inspection window arranged at a position allowing a user to inspect said hypodermic needle or needle hub.

The inspection window is a transparent inspection window.

In some embodiments, said inspection window is at least partly bordered by a non transparent part of said needle shield.

Consequently, the injection of the hypodermic syringe/needle may be hidden from the user, while the user still may clearly inspect whether a blood vessel has been hit. This may be especially helpful for the large group of patients suffering from trypanophobia.

The non transparent part may completely border said inspection window. The non transparent part may be opaque or translucent e.g. as frosted glass.

In some embodiments, said needle shield is an assembly assembled from a first part attached to said elongated main body, and a second part inserted into said first part.

In some embodiments, said first part of said needle shield is at least partly made of a transparent material and said second part is at least partly made of a non transparent material, wherein said second part comprises a through hole at least partly positioned in the portion of said second part being inserted into said first part, and wherein said through hole together with said first part forms said inspection window.

Consequently, a simple way of manufacturing a needle shield having an inspection window is provided. This may further allow the size of said inspection window to be easily changed e.g. by substituting the second part of the said needle shield with a new second part having a smaller or larger through hole.

In some embodiments, said housing further comprises a pressure sensor operatively connected to said light source, wherein said pressure sensor is configured to detect the contact pressure between said housing and the skin of said user, and wherein said injection device is configured to turn on said light source when a pressure above a predetermined first threshold is detected.

Consequently, the injection device may signal to the user when a suitable contact pressure between the injection device and the skin has been obtained. This may prevent the user from applying to much pressure whereby the risk of bone injections may be lowered.

The pressure sensor may be a button positioned at the bottom of said housing.

In some embodiments, said housing further comprises a pressure sensor, and wherein said injection device is configured to signal to said user that too much pressure is being applied when a pressure above a second threshold is detected by said pressure sensor.

The injection device may be configured to signal to the user that too much pressure is being applied by altering the light source (increasing or decreasing the light intensity), turning on or off an alternative light source, or signalling using audible sound emitted from a speaker. The second threshold may preferably be higher than the first threshold, thereby allowing the injection device to signal to a user both when too little and too much pressure is being applied.

Consequently, the risk of bone injections may be further lowered.

In some embodiments, said injection device further comprises a hypodermic syringe connected to a hypodermic needle through a needle hub, wherein said hypodermic syringe is arranged in said hypodermic syringe holder, and wherein said light source is arranged so that when it is activated and the movable element is in the injection position, the peak intensity of the resulting light beam is positioned at or below said needle hub thereby allowing a user to detect blood present in the needle hub or in the hypodermic needle.

For a large number of treatments, it is important to secure that the active substance is deposited subcutaneously or intramuscularly, and not delivered directly into a blood vessel since the effect then may be very short. Thus after a hypodermic syringe has been injected using an injector device, the user typically withdraw the plunger a small amount and watches the syringe for blood. If no blood is withdrawn into the syringe, the user knows that a suitable injection position has been chosen and may continue with injecting the active substance of the syringe by pushing the plunger.

However, for the large group of patients suffering from trypanophobia it may be very uncomfortable to be able to watch the injection of the needle into the skin.

Thus, it remains a problem to provide an injection device suitable for people suffering from trypanophobia allowing the user to detect whether the chosen injection position is suitable.

According to a fourth aspect, the invention relates to an injection device for injecting a hypodermic syringe along an injection direction, said injection direction defining an injection axis, wherein said injecting device comprises:
  a housing for being positioned at a user's skin, wherein said housing comprises an elongated main body and a needle shield attached to said elongated main body; and
  a movable element movably arranged relative to said housing between a retracted position and an injection position, wherein said movable element comprises a hypodermic syringe holder for holding a hypodermic syringe connected to a hypodermic needle through a needle hub;
wherein the injection device is configured to allow a user to manually operate the plunger of the hypodermic syringe attached to the hypodermic syringe holder and the needle shield comprises a transparent inspection window.

Consequently, the injection of the hypodermic syringe/needle may be hidden from the user, while the user still may clearly inspect whether a blood vessel has been hit. This may be especially helpful for the large group of patients suffering from trypanophobia.

In some embodiments, a portion of the movable element is arranged to slide at a first outer surface of said housing.

The inspection window may covered with a transparent material e.g. such as a transparent glass or plastic material. Alternatively, the inspection window may be an opening in the needle shield.

In some embodiments, said inspection window is arranged at a position allowing a user to inspect said hypodermic needle or needle hub, when said movable element is in the injection position.

In some embodiments, said housing comprises a planar contact surface for being positioned at the skin, wherein said inspection window is arranged with a distance to said planar contact surface between 0 cm and 2 cm, 0 cm and 1.5 cm, or 0 cm and 1 cm.

The distance from the inspection window to the planar contact surface is measured from the part of the inspection window being closest to the planar contact surface.

In some embodiments, the widest width of said inspection window is between 0.2 cm and 4 cm, 0.2 cm and 3 cm, or 0.5 cm and 2 cm.

Consequently, by having an inspection window with a limited size, the view of the injection through the inspection window may be correspondingly limited.

In some embodiments, the inspection window is arranged at the side of the needle shield.

In some embodiments, the needle shield further comprises a second inspection window positioned opposite to said (first) inspection window.

The second inspection window may have the same size and shape as the (first) inspection window. The second inspection window may be positioned at the same height as the (first) inspection window i.e. there may be a line of sight going through the centre part of said (first) inspection window and the centre part of said second inspection window, said line of sight being perpendicular to said injection axis.

Consequently, by having two inspection windows the injection device may be more freely handled by the user. This further allows a single injection device to be used by both left handed and right handed users. This allows the production costs of the product to be lowered.

In some embodiments, said inspection window is at least partly bordered by a non transparent part of said needle shield.

The non transparent part may be opaque or translucent e.g. as frosted glass.

In some embodiments, the non transparent part is completely bordering said inspection window. In some embodiments, said needle shield is an assembly assembled from a first part attached to said elongated main body, and a second part attached to said first part. In some embodiments, said needle shield is an assembly assembled from a first part attached to said elongated main body, and a second part inserted into said first part.

In some embodiments, said first part of said needle shield is at least partly made of a transparent material and said second part is at least partly made of a non transparent material, wherein said second part comprises a through hole at least partly positioned in the portion of said second part being inserted into said first part, and wherein said through hole together with said first part forms said inspection window.

Consequently, a simple way manufacturing a needle shield having an inspection window is provided. This may further allow the size of said inspection window to be easily changed e.g. by substituting the second part of the said needle shield with a new second part having a smaller or larger through hole.

In some embodiments, the needle shield is arranged so that the tip of a hypodermic needle of a hypodermic syringe attached to said hypodermic syringe holder is positioned completely inside the needle shield when the movable element is in the retracted position, and wherein said movable element can be retracted from the injection position to the retracted position.

Consequently, the needle tip may be at least partly hidden from the user. This may further reduce the stress for users suffering from trypanophobia.

In some embodiments, said housing comprises a gripping zone, said needle shield forms part of said gripping zone and wherein said gripping zone is configured to allow a user to safely hold said injection device at any position of said gripping zone while a hypodermic syringe is being injected by said injection device.

In some embodiments, said needle shield comprises grip elements configured to improve the grip of the needle shield, wherein said grip elements limits the transparency of the needle shield.

The grip elements may be small protrusions configured to improve the grip.

The inspection window thus further allows the needle shield to be fitted with features related to In some embodiments, said injection device further comprises a hypodermic syringe connected to a hypodermic needle through a needle hub, wherein said hypodermic syringe is arranged in said hypodermic syringe holder.

In some embodiments, said first part of said needle shield is at least partly made of a transparent material and said second part is at least partly made of a non transparent material, wherein said second part comprises a through hole at least partly positioned in the portion of said second part being inserted into said first part, and wherein said through hole together with said first part forms said inspection window.

According to a fifth aspect the invention relates to a method of injecting a hypodermic syringe, comprising:
obtaining an injection device as disclosed in relation to the first aspect of the invention, the second aspect of the invention, the third aspect of the invention, the fourth aspect of the invention, the seventh aspect of the invention, the eight aspect of the invention, the ninth aspect of the invention, or the tenth aspect of the invention with the movable element in the retracted position;
arranging a hypodermic syringe (having a hypodermic needle attached) in the hypodermic syringe holder;
positioning the injection device at the skin of a patient;
pushing a release mechanism on the injection device, whereby the movable element moves to said injection position and the hypodermic syringe is injected.

In some embodiments, the release mechanism is being pushed while the injection device is being held in the lower third part of the housing.

The injection may be performed on a location and with a depth securing that it does not result in a substantial health risk especially when carried out with the required expertise.

According to a sixth aspect, the invention relates to a method of injecting a substance carried in a hypodermic syringe into a patient, comprising:
obtaining an injection device as disclose in relation to the first aspect of the invention, the second aspect of the invention, the third aspect of the invention, the fourth aspect of the invention, the seventh aspect of the invention, the eight aspect of the invention, the ninth aspect of the invention, or the tenth aspect of the invention with the movable element in the retracted position;
arranging a hypodermic syringe (having a hypodermic needle attached) in the hypodermic syringe holder;
positioning the injection device at the skin of a patient;
pushing a release mechanism on the injection device, whereby the movable element moves to said injection position and the hypodermic syringe is injected;
manually, pushing the plunger of the hypodermic syringe, whereby the content of the hypodermic syringe is injected.

In some embodiments, the release mechanism is being pushed while the injection device is being held in the lower third part of the housing.

In some embodiments, the method further comprises the steps of:
retracting the movable element using a handle of the injection device, from the injection position to the retracted position, whereby the tip of the hypodermic needle is positioned completely inside the needle shield thereby protecting the user from being stung;

According to a seventh aspect, the invention relates to an injection device for injecting a hypodermic syringe along an injection direction defining an injection axis, wherein said injection device comprises:
a housing for being positioned at a user's skin, wherein said housing comprises a first tubular element having an upper opening;
a movable element movably arranged relative to said housing between a retracted position and an injection position, wherein said movable element comprises a hypodermic syringe holder for holding a hypodermic syringe and a first portion arranged to slide inside said first tubular element of said housing;
a spring connecting said movable element with said housing, wherein said spring, when released, is configured to move said movable element from said retracted position to said injection position; and
a release mechanism configured to allow a user to release said spring;
wherein said first portion of said movable element comprises an elongated opening, said release mechanism is movably arranged between a gripping position and a release position along a release mechanism axis and is partly inserted into said elongated opening, and when said movable element is in said retracted position, said release mechanism is arranged to release said spring by being moved from said gripping position to said release position.

Consequently, by providing a release mechanism that releases the spring by being moved along an axis, a release mechanism that is easy and safe to operate is provided.

The housing and/or the movable element may be made of plastic. The end of the first tubular element facing the skin of the user may be closed. Thus in use the upper opening of the first tubular element faces away from the skin of the user. The housing and the movable element may be practically non-deformable during normal use, i.e. the housing and the movable element may deform less than 5% during normal use. The tubular element may have a round or rectangular cross-section. The syringe holder may comprise a first set of gripping arms and a second set of gripping arms. The syringe holder may be detachably connected to the movable element, whereby it can be exchanged allowing the same injection device to be used together with different sized hypodermic syringes. The release mechanism may be a single element or an assembly of a number of elements. The elongated opening in the movable element may be a through hole or a concave portion.

The release mechanism is partly inserted into said elongated opening i.e. the release mechanism is inserted in said elongated opening but not completely enclosed within the elongated opening. However, if the elongated opening is a through hole, the release mechanism may extend through said through hole.

The spring may be any kind of spring such as a mechanical spring or a gas spring. The spring may be a compression spring or an expansion spring. The first portion of the movable element may comprise a disc having an outer surface interacting with the spring. The disc may form the distal end of the first portion of the movable element. The disc may have any shape such as circular or rectangular. The spring may be a compression spring i.e. a spring that when compressed stores mechanical energy. The compression spring may surround a part of the first portion of the movable element, and have a first end that abuts a first upper surface of said disc. The upper surface of said disc is the surface that faces away from the user when the injection device is positioned at the skin of the user. Thus when the movable element is in the retracted position the compression spring is compressed and thereby stores mechanical energy that can be used to move said movable element from said retracted position to said injection position whereby a hypodermic syringe attached to said hypodermic syringe holder may be injected. The housing may further comprise a second tubular element inserted into the top of said first tubular element, and wherein said movable element extends out of said second tubular element. The second tubular element may be permanently attached to the first tubular element. The second tubular element may be attached using an adhesive and/or a press fit i.e. a frictional fit.

In some embodiments, the spring is a compression spring that surrounds a part of the first portion of the movable element, and has a first end that abuts a first upper surface of said disc, and a second end that abuts a lower surface of the second tubular element.

In some embodiments, the movable element further comprises a second portion arranged to slide at a first outer surface of said housing, and a connection portion connecting said first portion with said second portion, wherein said movable element extends out of said upper opening of said first tubular element.

The second portion of the movable element may slide at a first outer surface of the first tubular element or another element of the housing e.g. an element attached to the first tubular element. The movable element may have a U-shape, wherein the first portion is the first leg of the U and the second portion is the second leg of the U and the connection portion is the bottom part of the U. The first portion and the second portion of the movable element may have an approximately equal length or they may differ in length. The syringe holder may be connected to the second portion of the movable element.

In some embodiments, said housing comprises a first side opening, said release mechanism is extending through said first side opening and comprises a contact surface that faces away from the housing, wherein said release mechanism is configured to be moved from said gripping position to said release position in response to a user pushing on said contact surface.

Consequently, an easy way of releasing the spring is provided.

The first side opening may be a through hole in the first tubular element. The second tubular element may further comprise a first side opening aligned with the first side opening of the first tubular element, wherein the release mechanism is further extending through said first side opening in said second tubular element.

In some embodiments, said release mechanism axis is perpendicular to said injection axis.

This allows the user to release the spring without having to press the injection device into the skin of the user. Consequently, the risk of the injection device sliding on the skin is reduced.

Furthermore, when the injection device is used by professional medical personnel the patient does not get a warning immediately before the injection as the injection device is not pressed towards the skin or twisted. This will make the experience more pleasant for the patients, especially patients suffering from trypanophobia.

In some embodiments, said release mechanism comprises a first portion and a second portion, said second portion abutting said movable element inside said elongated opening at an internal contact surface, and said spring pushing said internal contact surface towards said second portion, when said release mechanism is in said gripping position and said movable element is in said retracted position, and wherein said release mechanism is configured so that, when it is moved from said gripping position to said release position, said second portion no longer abuts said internal contact surface, whereby said spring is released.

Consequently, the spring may be released without having to completely remove the release mechanism from the movable element. This makes the release mechanism easier to operate and allows it to be easily re-used i.e. the injection device may be used to inject a plurality of hypodermic syringes.

The elongated opening of the movable element may be a through hole or a concave portion. The first portion and the second portion may each be an element that together as an assembly forms the release mechanism. Alternatively, the first portion and the second portion may be different portions of a single element. The elongated opening of the movable element may slide over the first portion of the release mechanism, when it is moved from the retracted position to the release position.

In some embodiments, said elongated opening comprises along the injection axis a first zone at a lower end of the elongated opening and a second zone positioned next to the first zone, said release mechanism being positioned in said first zone when the movable element is in the retracted position and in said second zone when the movable element is moving towards the injection position wherein;
  the elongated opening, at the first zone, along the release mechanism axis has a part with a first width and a part with a second width, said first width being larger than the width of the first portion of the release mechanism but smaller than the width of the second portion of the release mechanism, said second width being larger than the width of the second portion of the release mechanism;
  the elongated opening, at the second zone, along the release mechanism axis has a part with a third width and a part with a fourth width, said third width being larger than the width of the first portion of the release mechanism but smaller than the width of the second portion of the release mechanism, said fourth width being larger than the width of the second portion of the release mechanism;
  said second width extending along a longer part of the release mechanism axis than said fourth width, and wherein the internal contact surface constitutes at least a part of the interface between the first zone and the second zone whereby said second portion of the release mechanism is arranged in said part of the second zone having the fourth width, when the movable element is moving toward the injection position.

The first, second, third and fourth width, and the width of the first portion and the second portion are measured along an axis being perpendicular to both the injection axis and the release mechanism axis. This first width and the third width may be equal. Correspondingly, the second width and the fourth width may be equal. The lower end of the elongated opening is the end being closest to the skin of the user, when the injection device is position at the skin of the user.

In some embodiments, said injection device further comprise a locking mechanism, said locking mechanism being movably arranged between a locked position and an unlocked position along a locking mechanism axis, wherein said locking mechanism is configured to, when it is positioned in the locked position, prevent said release mechanism from being moved from said gripping position to said release position.

Consequently, a safer injection device is provided as unintentional release of the spring may be avoided.

The locking mechanism may be a single element or an assembly of a plurality of elements. The locking mechanism axis may be parallel with the injection axis. The locking mechanism may be moved in a direction towards the distal end of the injection device when it is moved from said locked position to said un-locked position i.e. the end of the injection device configured to rest on the skin of the user.

In some embodiments, said locking mechanism is slidably arranged in a second side opening of said housing, said second side opening being opposite to said first side opening, said locking mechanism comprising a blocking surface facing the housing, said blocking surface being aligned with said release mechanism axis when said locking mechanism is in the locked position and unaligned with said release mechanism axis when said locking mechanism is in said un-locked position, and wherein said elongated opening in said movable element is an elongated through hole, said release mechanism is arranged so that it in said release position is extending through said elongated through hole and further extends past said blocking surface.

Consequently, a simple and effective locking mechanism is provided.

The locking mechanism may comprise an opening arranged next to the blocking surface, wherein said release mechanism is arranged so that in said release position, it is extending through said elongated through hole of the movable element and further extends into said opening. The opening in the locking mechanism may be a through hole.

In some embodiments, said movable element is configured to, when being manually moved from said injection position to said retracted position, cause said locking mechanism to move from said un-locked position to said locked position.

Thus, an unintentional release of the spring after an injection has been made may be prevented. This especially important, when the injection device is used by medical professionals as the hypodermic syringe may be contaminated with infectious diseases. Consequently, a safer injection device is provided.

In some embodiments, said housing further comprises a needle shield.

The needle shield may be arranged so that the tip of a hypodermic needle of a hypodermic syringe attached to said hypodermic syringe holder is positioned inside the needle shield when the movable element is in the retracted position. The needle shield may be a tubular needle shield. The tubular needle shield comprises a first opening facing a user's skin when the injection device is positioned at the skin of the user. The housing may comprise a planar contact surface for being positioned at a user's skin, wherein the first opening forms part of said planar contact surface.

By having a needle shield the user may be protected from being stung by a hypodermic needle, when the movable element is in the retracted position.

Thus, the combination of a locking mechanism that is moved to the locked position when the movable element is being moved from said injection position to said retracted position and a needle shield as specified above provide an very safe injection device. The injection device may be used in to following manner:

A hypodermic syringe is positioned in the hypodermic syringe holder;

The injection device is positioned at the skin of the user;

The locking mechanism is moved from the locked position to the un-locked position;

The release mechanism is moved from the gripping position to the release position, whereby the movable element is moved from the retracted position to the injection position injecting the hypodermic syringe;

The substance in the hypodermic syringe is injected;

The movable element is manually retracted from the injection position to the retracted position, whereby the locking mechanism is moved from the un-locked position to the locked position and the needle tip is completely positioned inside the needle shield.

Thus, the injection device comprising the contaminated hypodermic syringe may now safely be removed, without exposing the professional medical personnel the risk of being stung as the needle tip is completely positioned inside the needle shield. Further, as the locking mechanism has been moved to the locked position there is no risk of accidentally releasing the spring.

In some embodiments, said movable element comprises a disc, said locking mechanism at a first end facing said disc comprises a spring, and wherein said movable element is configured to, when being moved from said injection position to said retracted position, push on said locking mechanism spring causing said locking mechanism to move from said un-locked position to said locked position.

Consequently, by providing the locking mechanism with a spring, a more compact injection device may be provided as the space requirements of the locking mechanism may be reduced. If the locking mechanism does not comprises a spring, the movable elements needs to be able to move a significant distance past said retracted position, to be able to push the locking mechanism from said un-locked position to said locked position, and further allow said locking mechanism, when the movable element is in the retracted position, to move from said locked position to said un-locked position without interfering with the disc of the movable element.

In some embodiments, said locking mechanism is arranged so that said locking mechanism spring is partly compressed, when said movable element is in said retracted position and said locking mechanism is in said un-locked position, said locking mechanism spring providing a first force (F1) along said locking mechanism axis in a direction towards said locked position, and wherein said housing comprises a gripping member configured to prevent said locking mechanism to move from said un-locked position to said locked position unless a second force (F2) along said locking mechanism axis in a direction towards said locked position is acting on said locking mechanism, said second force (F2) being higher than said first force (F1), whereby said locking mechanism can stay at said un-locked position without assistance from the user.

Consequently, the injection device becomes easier to operate as the user only needs to perform a single task at a time e.g. firstly, un-lock the locking mechanism and the secondly press the contact surface of the release mechanism. This enables safe single handed operation of release mechanism and locking mechanism. The freed hand may be used to securely hold the device at the skin.

In some embodiments, said release mechanism is arranged to move from said release position to said gripping position when said movable element is moved from said injection position to said retracted position.

In some embodiments, said release mechanism is arranged to move from said release position to said gripping position by being pushed by said locking mechanism, when said locking mechanism is moved from said un-locked position to said locked position.

Consequently, said injection device may in an easy manner be re-used for performing further injection i.e. there is no need for complicated re-setting procedures.

The release mechanism may comprise a sloping surface that interacts with an edge of the locking mechanism, when the locking mechanism is moved from the un-locked position to the locked position, so that a force induced by the locking mechanism is acting on the release mechanism along the release mechanism axis.

According to an eighth aspect, the invention relates to an injection device for injecting a hypodermic syringe along an injection direction defining an injection axis, wherein said injection device comprises:
  a housing for being positioned at a user's skin;
  a movable element movably arranged relative to said housing between a retracted position and an injection position, wherein said movable element comprises a hypodermic syringe holder for holding a hypodermic syringe;
  a spring connecting said movable element with said housing, wherein said spring, when released, is configured to move said movable element from said retracted position to said injection position; and
  a release mechanism configured to allow a user to release said spring;
wherein said injection device further comprises a locking mechanism, said locking mechanism being movably arranged between a locked position and an un-locked position along a locking mechanism axis, wherein said locking mechanism is configured to, when it is positioned in the locked position, prevent said release mechanism from releasing said spring and wherein said movable element is configured to, when being moved from said injection position to said retracted position, cause said locking mechanism to move from said un-locked position to said locked position.

According to a ninth aspect, the invention relates to an injection device for injecting a hypodermic syringe along an injection direction, said injection direction defining an injection axis, wherein said injection device comprises:
  a housing for being positioned at a user's skin, wherein said housing comprises an elongated main body;
  a signalling unit for signalling a state to a user;
  a first sensor configured to detect contact between the injection device and the skin of the user; and
  a movable element movably arranged relative to said housing between a retracted position and an injection position, wherein said movable element comprises a hypodermic syringe holder for holding a hypodermic syringe;
wherein said first sensor is operatively connected to said signalling unit and said injection device is configured to, after said first sensor has detected contact between the injection device and the skin of the user, control said signalling unit to signal to the user that the injection device is ready for injecting a hypodermic syringe.

Consequently, the user may know when the injection device is safely arranged at the skin before the injection is initiated.

The first signalling unit may be any unit capable of generating a signalling that the user can perceive such as an audio signal or a visual signal. The first sensor may be a temperature sensor, impedence sensor, or a pressure sensor. The injection device may be an injection device as disclosed in relation to aspect 1 to 4, 7, or 9 to 10 of the invention e.g. the housing may a housing as disclosed in relation to aspect 1 to 4, 7, or 9 to 10 of the invention and the movable element may be a movable element as disclosed in relation to aspect 1 to 4, 7, or 9 to 10 of the invention. The injection device may be configured to control the signalling unit to start signalling to the user immediately after the first sensor has determined contact or after a specific type of contact has been determined e.g. a specific contact pressure.

The injection device may comprise a processing unit operatively connected to the first sensor and the signalling unit wherein said processing unit is configured to control said signalling unit to signal to the user that the injection device is ready for injecting a hypodermic syringe. Alternatively, the injection device may be mechanically configured to control said signalling unit to signal to the user that the injection device is ready for injecting a hypodermic syringe after said first sensor has detected contact between the injection device and the skin of the user.

In some embodiments, said first sensor is a pressure sensor configured to detect the contact pressure between said housing and the skin of said user; and said injection device is configured to, when a contact a pressure above a predetermined first threshold is detected, control said signalling unit to signal to the user that the injection device is ready for injecting a hypodermic syringe.

In some embodiments, the signalling unit is one or more light source(s).

In some embodiments, the one or more light source(s) is configured to signal to the user that the injection device is ready for injecting a hypodermic syringe by:
  starting to emit light;
  stopping with emitting light;
  starting to blink;
  changing a blinking frequency; or
  changing colour.

In some embodiments, the signalling unit is a speaker.

In some embodiments, the speaker is configured to signal to the user that a sufficient contact pressure between said housing and the skin of said user is present by:
  starting to play sound;
  stopping with playing a sound;
  changing a sound.

In some embodiments, said pressure sensor is arranged at the bottom of the housing.

In some embodiments, the pressure sensor comprises a button movably arranged between a first position and a second position, a pressure sensor spring, a power source, and an electric switch configured to make or break a first electric circuit between said signalling unit and said power source, wherein said electric switch is configured to make said first electric circuit when said button is at said second position; said pressure sensor spring is arranged to keep the button away from said second position until a contact pressure larger than said first threshold is acting on said button.

In some embodiments, the injection device is further configured to, when a contact at a pressure above a predetermined second threshold is detected, control said signalling unit to signal to the user that the contact pressure between said housing and the skin of said user is to large.

Consequently, the safety of the injections may be improved as the risk of injecting the hypodermic syringe in bone or critical organs may be prevented.

In some embodiments, the injection device is further configured to, when a contact at a pressure above a predetermined second threshold is detected, lock said movable element in said retracted position.

Consequently, unsafe injection caused by too large a contact pressure may entirely be prevented According to a tenth aspect, the invention relates to an injection device for injecting a hypodermic syringe along an injection direction defining an injection axis, wherein said injecting device comprises:
- a housing having a planar contact surface for being positioned at the skin, said housing comprising an elongated main body and a needle shield having a first side and a second side, said second side being opposite to said first side, wherein said needle shield is attached to the elongated main body at said first side; and
- a movable element movably arranged relative to said housing between a retracted position and an injection position, wherein said movable element comprises a hypodermic syringe holder for holding a hypodermic syringe;

wherein said planar contact surface is arranged in a plane being angled with an angle below 80 degrees relative to said injection axis, and said needle shield comprises a concave portion for receiving a finger, said concave portion being configured to allow a user to securely hold said injection device at the skin using said finger.

Consequently, by providing an injection device that can be securely held at the skin using a single finger angled injections may be performed safer, as the hand holding the injection device is less likely to interfere with the movable element.

Furthermore, it becomes easier to perform injections at steep angles, as there no longer is a need for gripping the injection device at the side of the injection device facing the skin (where it may be difficult to fit a finger).

The injection device may be an injection device as disclosed in relation to aspect 1 to 4 or 7 to 9 of the invention e.g. the housing may a housing as disclosed in relation to aspect 1 to 4 or 7 to 9 of the invention and the movable element may be a movable element as disclosed in relation to aspect 1 to 4 or 7 to 9 of the invention.

In some embodiments, said concave portion is formed in said second side of said needle shield.

In some embodiments, said planar contact surface is arranged in a plane being angled with an angle below 75 degrees and above 30 degrees relative to said injection axis.

In some embodiments, said planar contact surface is arranged in a plane being angled with an angle of approximately 45 degrees relative to said injection axis.

In some embodiments, the widest width of the concave portion is at least 1 cm.

In some embodiments, the widest width of the concave portion is no more than 3 cm.

In some embodiments, the widest width of the concave portion is no more than 2 cm.

In some embodiments, the concave portion has a depth of at least 1 mm, 1.5 mm, or 2 mm.

Consequently, a single finger may be arranged in the concave portion.

In some embodiments, said needle shield and said elongated main body is integrally moulded.

In some embodiments, said needle shield comprises an inspection window arranged at a position allowing a user to inspect said hypodermic needle or needle hub while a finger is arranged at the concave portion.

In some embodiments, the injection device further comprises:
- a spring connecting said movable element with said housing, wherein said spring, when released, is configured to move said movable element from said retracted position to said injection position; and
- a release mechanism configured to allow a user to release said spring;

wherein the elongated main body of said housing is a first tubular element, said movable element comprises a first portion arranged to slide inside said first tubular element of said housing, said first portion of said movable element comprises an elongated opening, said release mechanism is movably arranged between a gripping position and a release position along a release mechanism axis and is partly inserted into said elongated opening, and when said movable element is in said retracted position, said release mechanism is arranged to release said spring by being moved from said gripping position to said release position.

In some embodiments, said release mechanism axis is perpendicular to said injection axis.

Consequently, by having a injection device that can be secured to the skin using a single finger it becomes easier to operate the release mechanism.

In some embodiments, said injection device further comprises a locking mechanism, said locking mechanism being movably arranged between a locked position and an unlocked position along a locking mechanism axis, wherein said locking mechanism is configured to, when it is positioned in the locked position, prevent said release mechanism from being moved from said gripping position to said release position.

The different aspects of the present invention can be implemented in different ways including as injection devices and methods of using such injection devices, described above and in the following, each yielding one or more of the benefits and advantages described in connection with at least one of the aspects described above, and each having one or more preferred embodiments corresponding to the preferred embodiments described in connection with at least one of the aspects described above and/or disclosed in the dependent claims. Furthermore, it will be appreciated that embodiments described in connection with one of the aspects described herein may equally be applied to the other aspects.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein:

FIG. 1-7 show different views of an injection device according to an embodiment of the present invention.

FIG. 1 shows a perspective view,

FIG. 2 shows a side view with the movable element in the injection position,

FIG. 3 shows a side view with the movable element in the retracted position,

FIG. 4 shows a central cross-section with the movable element in the retracted position;

FIG. 5 shows a central cross-section with the movable element in the injection position;

FIG. 6 shows a cross-sections along the line 191 shown in FIG. 5, and

FIG. 7 shows an exploded view.

FIG. 10 shows a perspective view,

FIG. 11 shows a side view with the movable element in the injection position,

FIG. 12 shows a side view with the movable element in the retracted position,

FIG. 13 shows a central cross-section with the movable element in the retracted position;

FIG. 14 shows a central cross-section with the movable element in the injection position, and FIG. 15 shows an exploded view.

FIG. 18 shows a perspective view,

FIG. 19 shows a side view with the movable element in the injection position,

FIG. 20 shows a side view with the movable element in the retracted position,

FIG. 21 shows a central cross-section with the movable element in the retracted position, FIG. 22 shows a central cross-section with the movable element in the injection position, and FIG. 23 shows an exploded view.

FIGS. 26-32b show different views of parts of an injection device according to an embodiment of the present invention.

FIG. 26 shows an exploded view,

FIG. 27 shows a perspective view,

FIG. 30 a shows a side view,

FIG. 30b shows a cross-sectional view,

FIG. 32b shows a cross-sectional view.

DETAILED DESCRIPTION

In the following description, reference is made to the accompanying figures, which show by way of illustration how the invention may be practiced.

Figure 4:
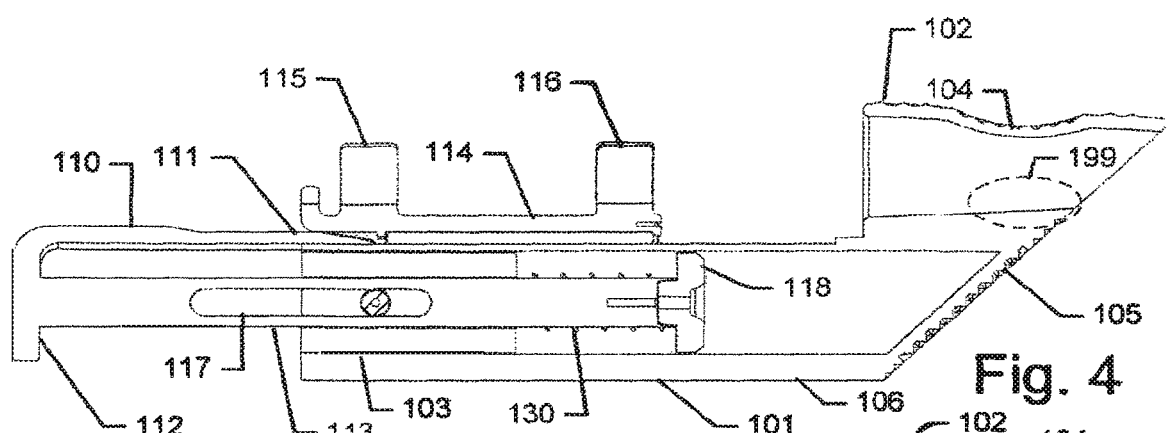
Figure 5:
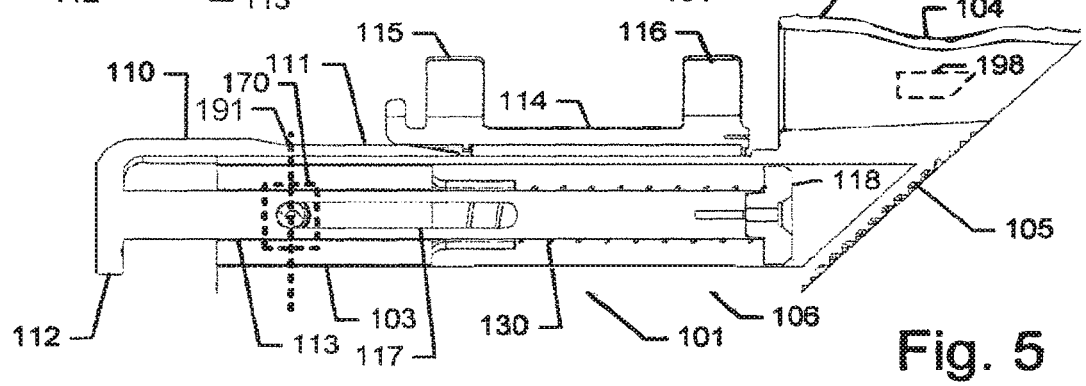
Figure 6:
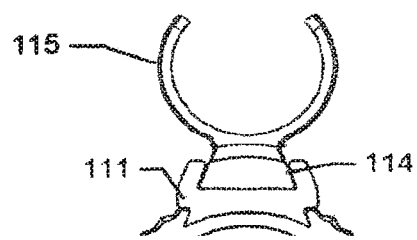
Figure 7:
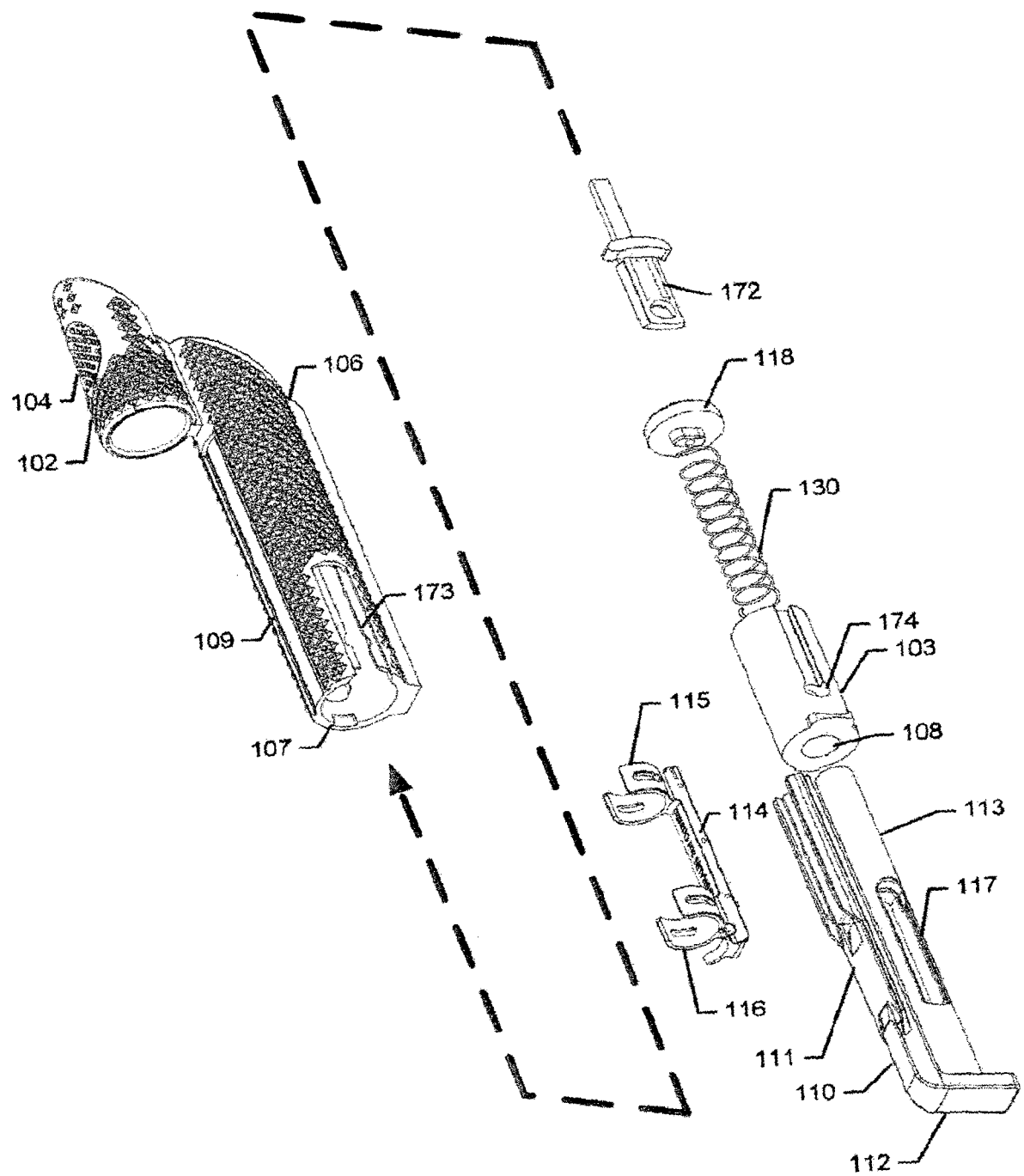

FIGS. 1-7 show different views of an injection device 100 for injecting a hypodermic syringe along an injection direction defining an injection axis 180 according to an embodiment of the present invention. In the following reference will be made to FIGS. 1-7. The injection device 100 comprises a housing 101 and a movable element 110 movable relative to said housing 101 between a retracted position and an injection position. FIG. 1 shows a perspective view, FIG. 2 shows a side view with the movable element in the injection position, FIG. 3 shows a side view with the movable element in the retracted position, FIG. 4 shows a central cross-section with the movable element in the retracted position, FIG. 5 shows a central cross-section with the movable element in the injection position, 6 shows a cross-sections along the line 190 shown in FIG. 5, and FIG. 7 shows an exploded view. The movable element 110 comprises a syringe holder 114 for holding a syringe. The syringe holder comprises a first set of gripping arms 115 and a second set of gripping arm 116. The housing 101 comprises an elongated main body, which in this embodiment is a first tubular element 106.

The movable element 110 comprises a first portion 113 arranged to slide inside the first tubular element 106 of the housing 101, a second portion 111 arranged to slide at a first outer surface of the housing 101, and a connection portion 112 connecting the first portion 113 with the second portion 111, wherein the movable element 110 extends out of an upper opening 107 of the first tubular element 106.

This allows a user to more freely grip and handle the injection device 100 e.g. a gripping zone may be formed in the lower third part of the injection device 100 providing better control to the user.

The injection device 100 is configured so that when the movable element 110 is in the retracted position (see FIGS. 3 and 4) the first portion 113 is extending out of the first tubular element 106 through the upper opening 107 of the first tubular element 106, and when the movable element 110 is in the injection position (see FIGS. 2 and 5) the first portion 113 is entirely positioned inside the first tubular element 106 and the second portion 111 and the connection portion 112 are positioned entirely outside the housing 101. The first portion 112 of the movable element comprises an elongated through hole 117.

The first outer surface of the housing 101 comprises a groove 109 extending along the injection axis 180. The second portion 111 of the movable element 110 engages with the groove 109. The groove 109 comprises a first wall 141 and a second wall 142 that slope inwards, whereby the second portion 111 is prevented from moving in any other direction than along the injection axis 180. The connection portion 112 comprises a handle allowing a user, when the movable element 110 is in the injection position, to grip the movable element 110 and retracts the movable element 110 back into the retracted position.

The housing 101 further comprises a second tubular element 103 inserted into the top of the first tubular element 106. The movable element 110 extends out of the second tubular element 103. The movable element 110 is configured so that a part of the first portion 113 slides along an inner surface of the second tubular 103 element thereby providing additional mechanical stability i.e. the first portion 113 comprises a cylindrical element that approximately fits the inner diameter 108 of the second tubular element 103.

The injection device 100 further comprises a spring 130 connecting the movable element 110 with the housing 101. In this embodiment, the spring 130 is a compression spring i.e. a spring that when compressed stores mechanical energy.

The first portion 113 of the movable element 110 further comprises a disc 118 having an outer surface interacting with the spring 130. The disc 118 has a shape matching the shape of the inner surface of said first tubular element thereby providing further mechanical stability.

The spring 130 surrounds a part of the first portion 113 of the movable element 110 and has a first end that abuts a first upper surface of the disc 118 and a second end that abuts a lower surface of the second tubular element 103. Thus when the movable element 110 is in the retracted position, the spring is compressed and thereby stores mechanical energy that can be used to move the movable element 110 from the retracted position to the injection position whereby a hypodermic syringe attached to the hypodermic syringe holder may be injected.

The housing 101 comprises a planar contact surface 105 for being positioned at the skin, wherein the planar contact surface 105 is positioned in a plane 181 being angled with an angle 182 below 90 degrees relative to said injection axis 180.

The angle 182 between the planar contact surface 105 and the injection axis 180 is defined as the smaller of the two possible angels measurable between a plan and a line. In this specific embodiment the angle 182 is 45 degrees. An angle of 45 degrees may be suitable for making subcutaneous injections. The planar contact surface 105 comprises a plurality of protrusions for establishing a high frictional contact with the skin (see FIGS. 4 and 5).

The housing 101 further comprises a needle shield 102 attached to the first tubular element 106. The needle shield 102 in this embodiment is a tubular needle shield. The needle shield 102 forms part of a gripping zone 190 (as shown on FIG. 3). The gripping zone 190 comprises a first concave portion 104 suitable for receiving one finger. The first concave portion 104 has widest width 1001 and a depth 1002 (see FIG. 2). The gripping zone 190 is positioned in the lower third part of the housing 101. The gripping zone 190 is configured to allow a user to safely hold said injection device 100 at any position of said gripping zone while a hypodermic syringe is being injected.

In this embodiment, the first concave portion 104 is configured to allow a user to securely hold said injection device 100 at the skin with a single finger arranged in said first concave portion 104. The needle shield 102 comprises a first side 1003 and a second side 1004 opposite to the first side 1003 (see FIG. 3). The needle shield 102 is attached to the first tubular element 106 (elongated main body of the housing) at the first side 1003. In this particular embodiment, the needle shield 102 and the first tubular element 106 is integrally moulded and the first concave portion 104 is formed in the second side 1004 of the needle shield 102.

The movable element 110 is arranged in a manner relative to the housing 101 so that at least 65% of the outer circumference of any cross-section of the housing 101 being perpendicular to the injection axis 180 does not interact with the movable element 110 at any possible position of the movable element 110. Thus, a user may hold the injection device 100 at the skin with a single handed grip with a first finger positioned in the concave portion 104 and a second finger position on the housing 101 opposite of the concave portion 104 without risking interfering with the movement of the movable element 110. The needle shield has a minimum height 183. The minimum height is measured as the minimum width of the needle shield 102 along the injection axis 180.

The injection device 100 may comprise a light source 199 (only schematically shown on FIG. 4) wherein the light source 199 is arranged so that when it is activated and the movable element 110 is in the injection position, the peak intensity of the resulting light beam is positioned at or below the needle hub connecting an hypodermic needle with an hypodermic syringe attached to the hypodermic syringe holder 114, thereby allowing a user to detect blood present in the needle hub or in the hypodermic needle.

The injection device 100 may comprise an inspection window 198 (only schematically shown on FIG. 5) arranged at a position allowing a user to inspect said hypodermic needle or needle hub. Consequently, the injection of the hypodermic syringe/needle may be hidden from the user, while the user still may clearly inspect whether a blood vessel has been hit. This may be especially helpful for the large group of patients suffering from trypanophobia.

The needle shield 102 is arranged so that the tip of a hypodermic needle of a hypodermic syringe attached to said hypodermic syringe holder 114 is positioned completely inside the needle shield 102 when the movable element 110 is in the retracted position. The handle 112 further allows the movable element 110 to be manually retracted from the injection position to the retracted position.

The injection device 100 comprises a release mechanism 170 (only schematically shown on FIG. 5) for releasing the spring 170, whereby the movable 110 is moved from the retracted position to the injection position. The release mechanism may be a release mechanism as explained in relation to the seventh aspect of the invention, i.e. a release mechanism that is partly inserted into the through hole (117) of the movable element 110, wherein the release mechanism is movably arranged between a gripping position and a release position along a release mechanism axis.

The injection device 100 further comprises a locking mechanism 172. The locking mechanism 172 is movably arranged between a locked position and an un-locked position along a locking mechanism axis 175. The locking mechanism is configured to when it is positioned in the locked position prevent the release mechanism 170 from releasing the spring 130 e.g. by preventing the release mechanism 170 from being moved from the gripping position to the release position. This provides a safer injection device, as unintentional release of the spring may be prevented. In this embodiment, the locking mechanism axis 175 is parallel with the injection axis 180. The locking mechanism 172 is slidably arranged in a second side opening 173 (see FIG. 7). The locking mechanism is shown in the locked position in FIGS. 3 and 8, and in the un-locked position in FIGS. 1, 2 and 9. The locking mechanism 172 may be a locking mechanism as explained in relation to the seventh aspect of the invention.

Figure 8:
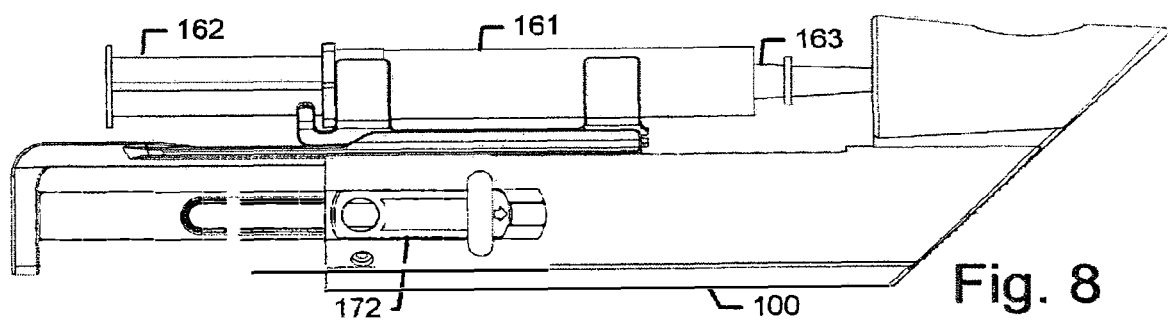
FIG. 8 shows a side view of an injection device comprising a hypodermic syringe with the movable element in the retracted position according to an embodiment of the present invention.
Figure 9:
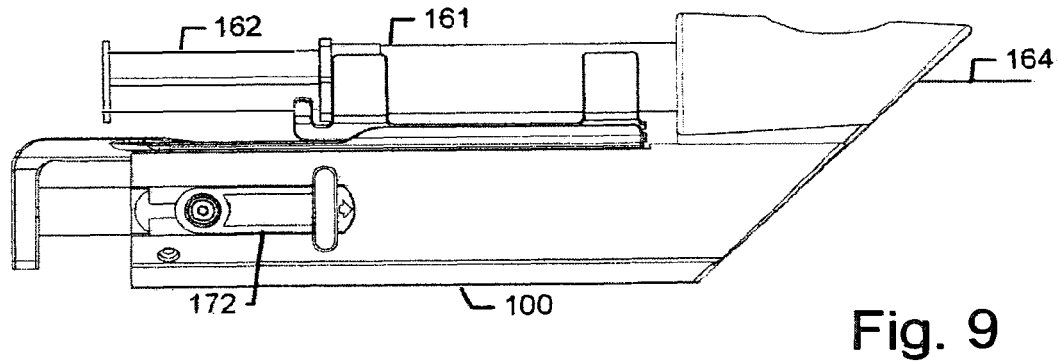
FIG. 9 shows a side view of an injection device comprising a hypodermic syringe with the movable element in the injection position according to an embodiment of the present invention.

FIGS. 8 and 9 shows an injection device 100 comprising a hypodermic syringe 161 with a plunger 162 according to an embodiment of the invention. FIG. 8 shows the injection device 100 with the movable element in the retracted position and FIG. 9 shows the injection device 100 with the movable element in the injection position. The injection device 100 is identical to the injection device shown in FIGS. 1 to 7. The hypodermic syringe 161 is connected to a hypodermic needle 164 through a needle hub 163.

Figure 10:
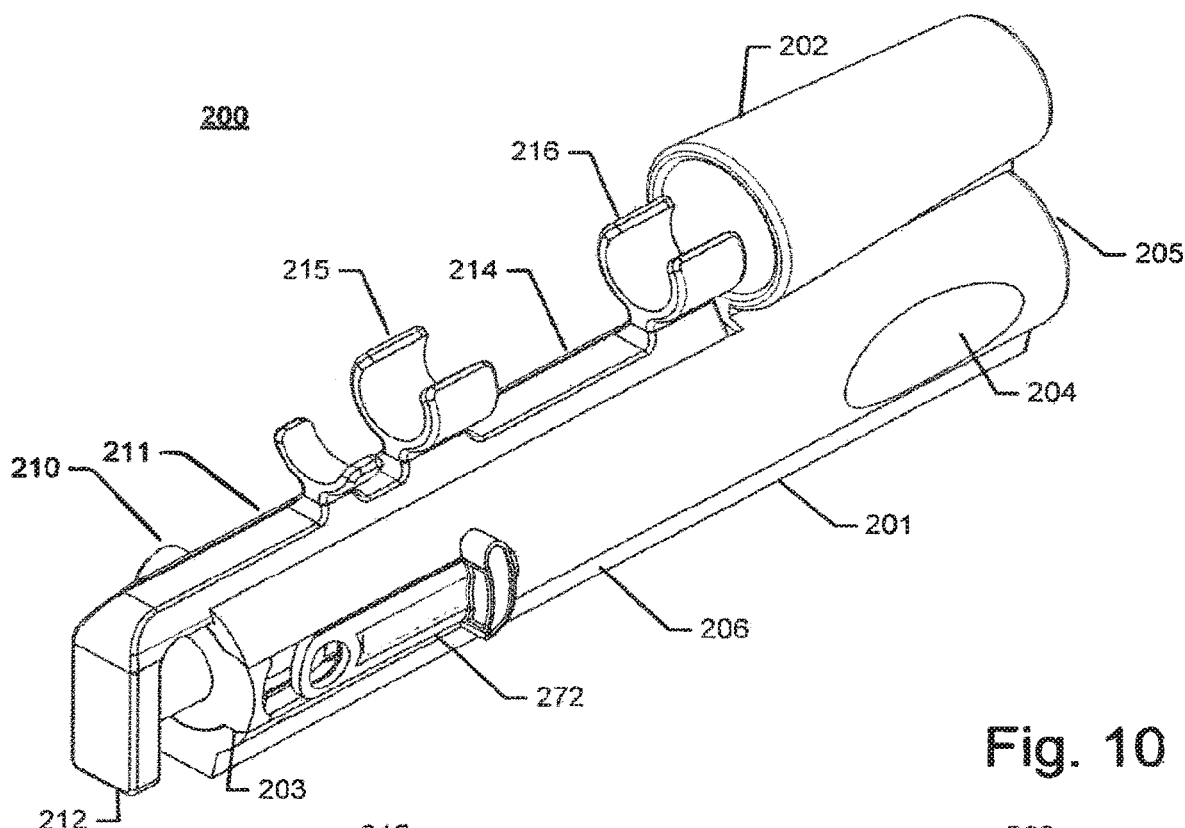
FIG. 10-15 show different views of an injection device according to an embodiment of the present invention.
Figure 11:
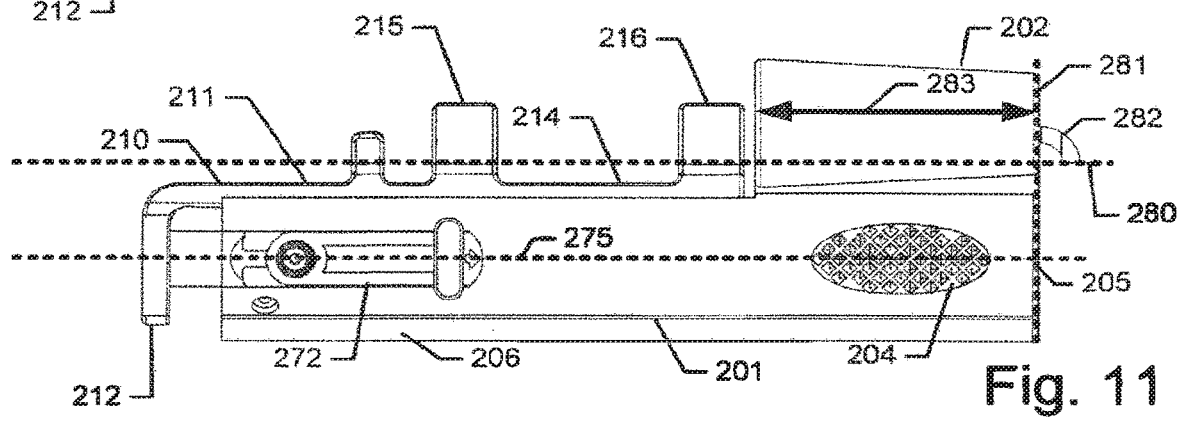
Figure 12:
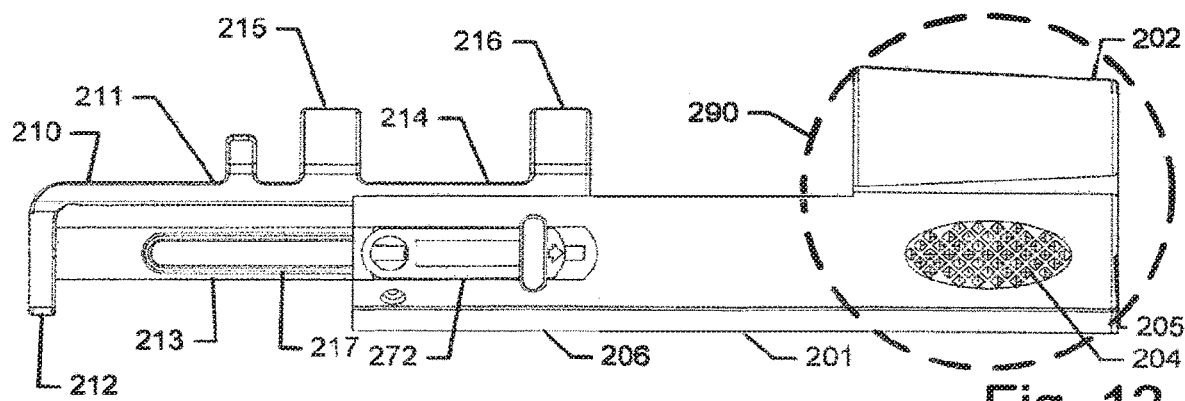
Figure 13:
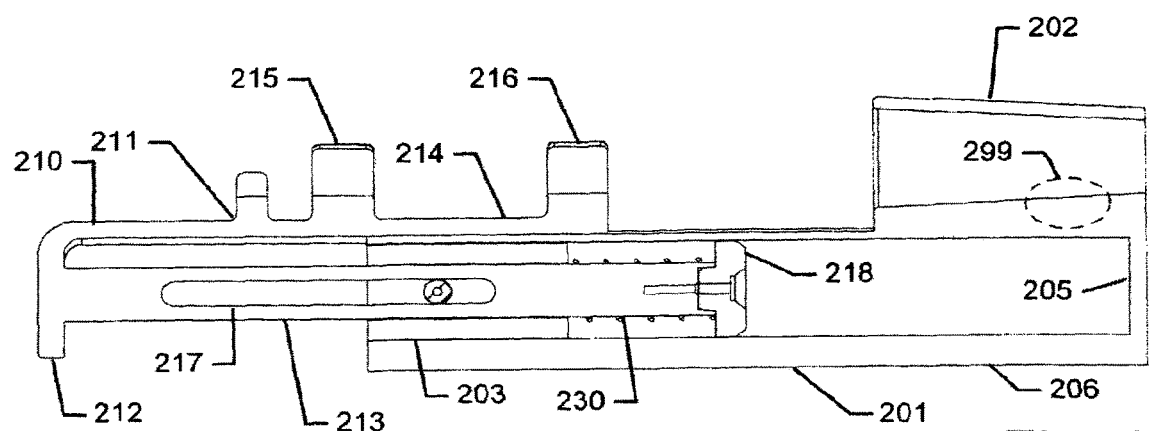
Figure 14:
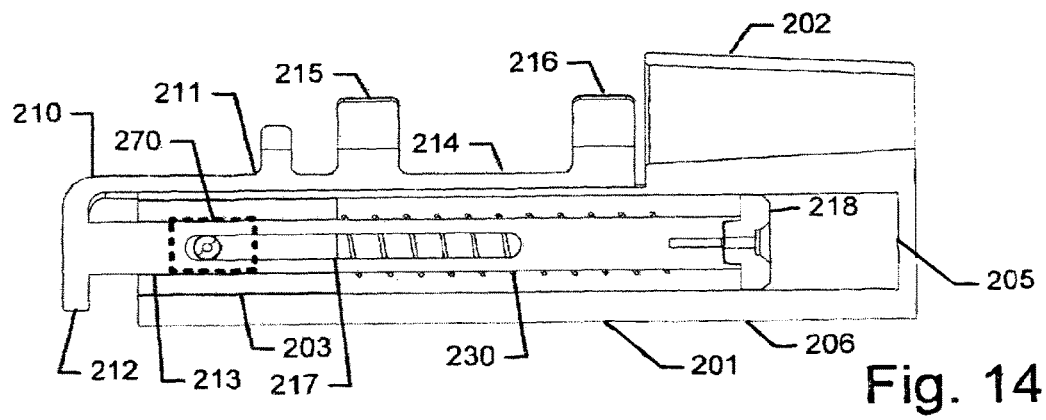
Figure 15:
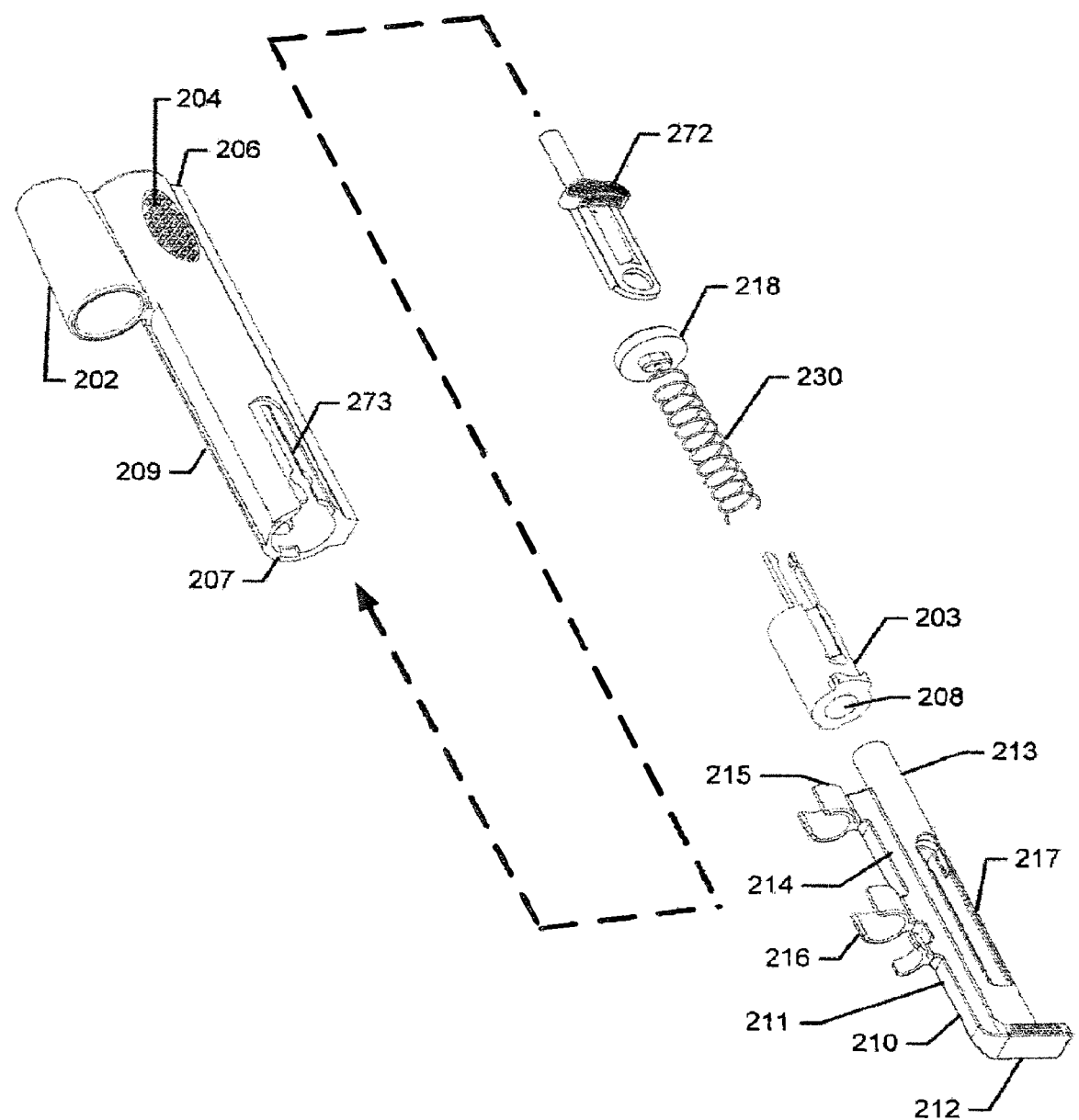

FIGS. 10-15 show different views of an injection device 200 for injecting a hypodermic syringe along an injection direction defining an injection axis 280 according to an embodiment of the present invention. In the following, reference will be made to FIGS. 10-15. The injection device 200 comprises a housing 201 and a movable element 210 movable relative to said housing 201 between a retracted position and an injection position. FIG. 10 shows a perspective view, FIG. 11 shows a side view with the movable element in the injection position, FIG. 12 shows a side view with the movable element in the retracted position, FIG. 13 shows a central cross-section with the movable element in the retracted position, FIG. 14 shows a central cross-section with the movable element in the injection position, and FIG. 15 shows an exploded view. The movable element 210 comprises a syringe holder 214 for holding a syringe; the syringe holder (214) comprises a first set of gripping arms 215 and a second set of gripping arms 216. The housing 201 comprises an elongated main body, which in this embodiment is a first tubular element 206.

The movable element 210 comprises a first portion 213 arranged to slide inside the first tubular element 206 of the housing 201, a second portion 211 arranged to slide at a first outer surface of the housing 201, and a connection portion 212 connecting the first portion 213 with the second portion 211, wherein the movable element 210 extends out of an upper opening 207 of the first tubular element 206.

This allows a user to more freely grip and handle the injection device 200 e.g. a gripping zone may be formed in the lower third part of the injection device 200 providing better control to the user.

The injection device 200 is configured so that when the movable element 210 is in the retracted position (see FIGS. 12 and 13) the first portion 213 is extending out of the first tubular element 206 through the upper opening 207 of the first tubular element 206, and when the movable element 210 is in the injection position (see FIGS. 11 and 14) the first portion 213 is entirely positioned inside the first tubular element 206 and the second portion 211 and the connection portion 212 are positioned entirely outside the housing 201. The first portion 213 of the movable element comprises an elongated through hole 217.

The first outer surface of the housing 201 comprises a groove 209 extending along the injection axis 180. The second portion 211 of the movable element 210 engages with the groove 209. The groove 209 comprises a first wall and a second wall that slope inwards, whereby the second portion 211 is prevented from moving in any other direction than along the injection axis 280.

The connection portion 212 comprises a handle allowing a user, when the movable element 210 is in the injection position, to grip the movable element 210 and retracts the movable element 210 back into the retracted position.

The housing 201 further comprises a second tubular element 203 inserted into the top of the first tubular element 206. The movable element 210 extends out of the second tubular element 203. The movable element 210 is configured so that a part of the first portion 213 slides along an inner surface of the second tubular element 203 hereby providing additional mechanical stability i.e. the first portion 213 comprises a cylindrical element that approximately fits the inner diameter 208 of the second tubular element 203.

The injection device 200 further comprises a spring 230 connecting the movable element 210 with the housing 201. In this embodiment the spring 230 is a compression spring i.e. a spring that when compressed stores mechanical energy. The first portion 213 of the movable element 210 further comprises a disc 218 having an outer surface interacting with the spring 230. The disc 218 has a shape matching the shape of the inner surface of said first tubular element thereby providing further mechanical stability.

The spring 230 surrounds a part of the first portion 213 of the movable element 210 and has a first end that abuts a first upper surface of the disc 218 and a second end that abuts a lower surface of the second tubular element 203. Thus when the movable element 210 is in the retracted position, the spring is compressed and thereby stores mechanical energy that can be used to move the movable element 210 from the retracted position to the injection position whereby a hypodermic syringe attached to the hypodermic syringe holder may be injected.

The housing 201 comprises a planar contact surface 205 for being positioned at the skin, wherein the planar contact surface 205 is positioned in a plane 281 being angled with an angle 282 of 90 degrees relative to said injection axis 280.

An angle of 90 degrees may be suitable for making intramuscular injections.

The housing 201 further comprises a needle shield 202 attached to the first tubular element 206. The needle shield 202 is in this embodiment a tubular needle shield. The needle shield 202 forms part of a gripping zone 290 (as shown on FIG. 12). The gripping zone 290 comprises a first concave portion 204, and a second concave portion (not seen in the figures) positioned opposite to the first concave portion. The first and the second concave portions are suitable for receiving one or more fingers. The gripping zone 290 is positioned in the lower third part of the housing 201. The gripping zone 290 is configured to allow a user to safely hold the injection device 200 at any position of said gripping zone while a hypodermic syringe is being injected.

The movable element 210 is arranged in a manner relative to the housing 206 so that at least 65% of the outer circumference of any cross-section of the housing 206 being perpendicular to the injection axis 280 does not interact with the movable element 210 at any possible position of the movable element 210. Thus a user may hold the injection device 200 at the skin with a single handed grip with a first finger positioned in the first concave portion 204 and a second finger position in the second concave portion without risking interfering with the movement of the movable element 210. The needle shield has a minimum height 283. The minimum height is measured as the minimum width of the needle shield 202 along the injection axis 280.

The injection device 200 may comprise a light source 299 (only schematically shown on FIG. 13) wherein the light source 299 is arranged so that when it is activated and the movable element 210 is in the injection position, the peak intensity of the resulting light beam is positioned at or below the needle hub connecting an hypodermic needle with an hypodermic syringe attached to the hypodermic syringe holder 214, thereby allowing a user to detect blood present in the needle hub or in the hypodermic needle.

The injection device 200 may comprise an inspection window 298 (only schematically shown on FIG. 17) arranged at a position allowing a user to inspect said hypodermic needle or needle hub. Consequently, the injection of the hypodermic syringe/needle may be hidden from the user, while the user still may clearly inspect whether a blood vessel has been hit. This may be especially helpful for the large group of patients suffering from trypanophobia.

The needle shield 202 is arranged so that the tip of a hypodermic needle of a hypodermic syringe attached to said hypodermic syringe holder 214 is positioned completely inside the needle shield 202 when the movable element 210 is in the retracted position. The handle of the connection portion 212 further allows the movable element 210 to be manually retracted from the injection position to the retracted position.

The injection device 200 comprises a release mechanism 270 (only schematically shown on FIG. 14) for releasing the spring 230, whereby the movable element 210 is moved from the retracted position to the injection position. The release mechanism may be a release mechanism as explained in relation to the seventh aspect of the invention. i.e. a release mechanism that is partly inserted into the through hole of the movable element 217, wherein the release mechanism is movably arranged between gripping position and a release position along a release mechanism axis.

The injection device 200 further comprises a locking mechanism 272. The locking mechanism 272 is movably arranged between a locked position and an un-locked position along a locking mechanism axis 175. The locking mechanism is configured to when it is positioned in the locked position prevent the release mechanism 270 from releasing the spring 230 e.g. by preventing the release mechanism 270 from being moved from the gripping position to the release position. This provides a safer injection device, as unintentional release of the spring may be prevented. In this embodiment, the locking mechanism axis 275 is parallel with the injection axis 280. The locking mechanism 275 is slidably arranged in a second side opening 273 of the housing 202. The locking mechanism is shown in the locked position in FIG. 12, and in the un-locked position in FIGS. 10 and 11. The locking mechanism 272 may be a locking mechanism as explained in relation to the seventh aspect of the invention.

Figure 16:
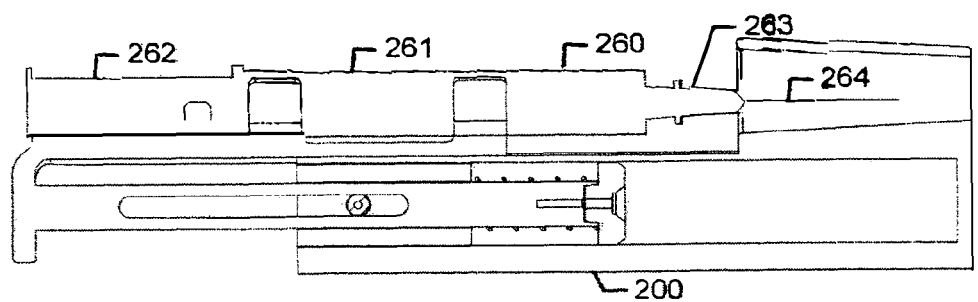
FIG. 16 shows a side view of an injection device comprising a hypodermic syringe with the movable element in the retracted position according to an embodiment of the present invention.
Figure 17:
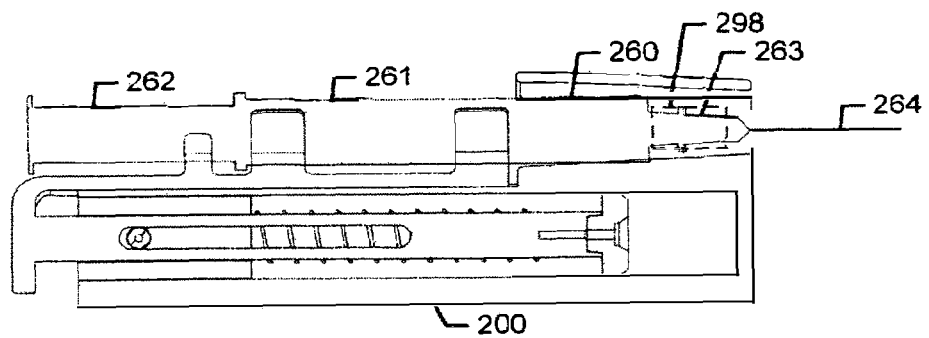
FIG. 17 shows a side view of an injection device comprising a hypodermic syringe with the movable element in the injection position according to an embodiment of the present invention.

FIGS. 16 and 17 shows an injection device 200 comprising a hypodermic syringe 261 having a barrel 260 and plunger 262 according to an embodiment of the invention. FIG. 16 shows the injection device 200 with the movable element in the retracted position and FIG. 17 shows the injection device 200 with the movable element in the injection position. The injection device 200 is identical to the injection device shown in FIGS. 10 to 15. The hypodermic syringe 261 is connected to a hypodermic needle 264 through a needle hub 263.

Figure 18:
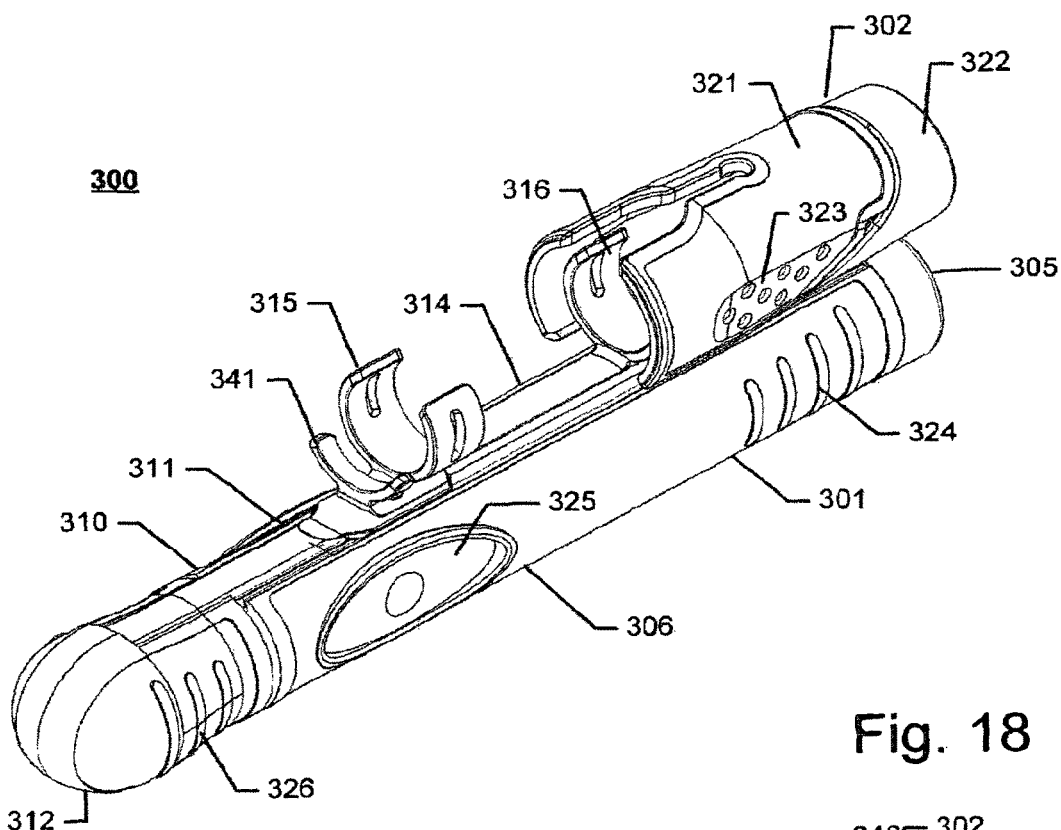
FIGS. 18-23 show different views of an injection device according to an embodiment of the present invention.
Figure 19:
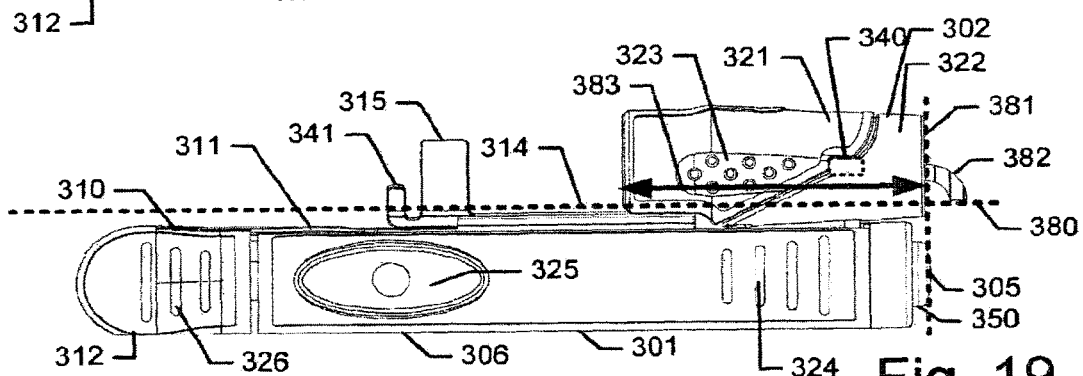
Figure 20:
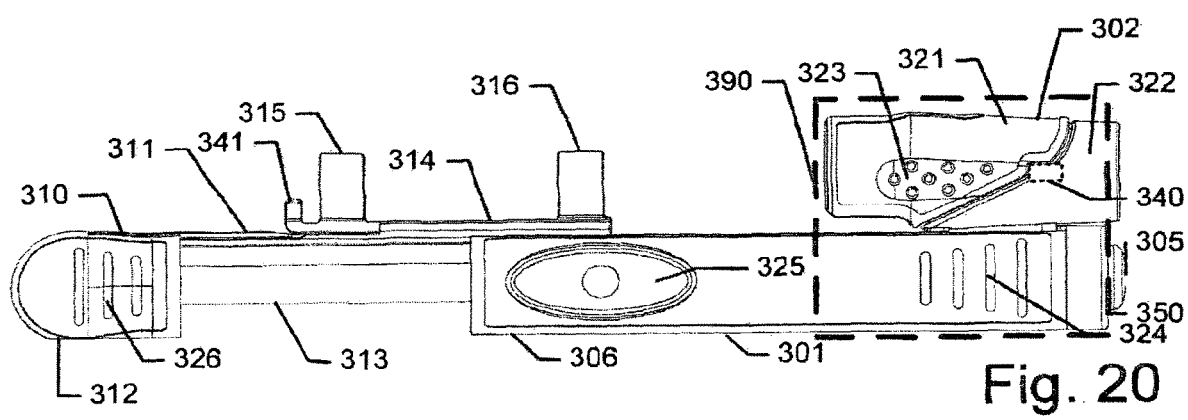
Figure 21:
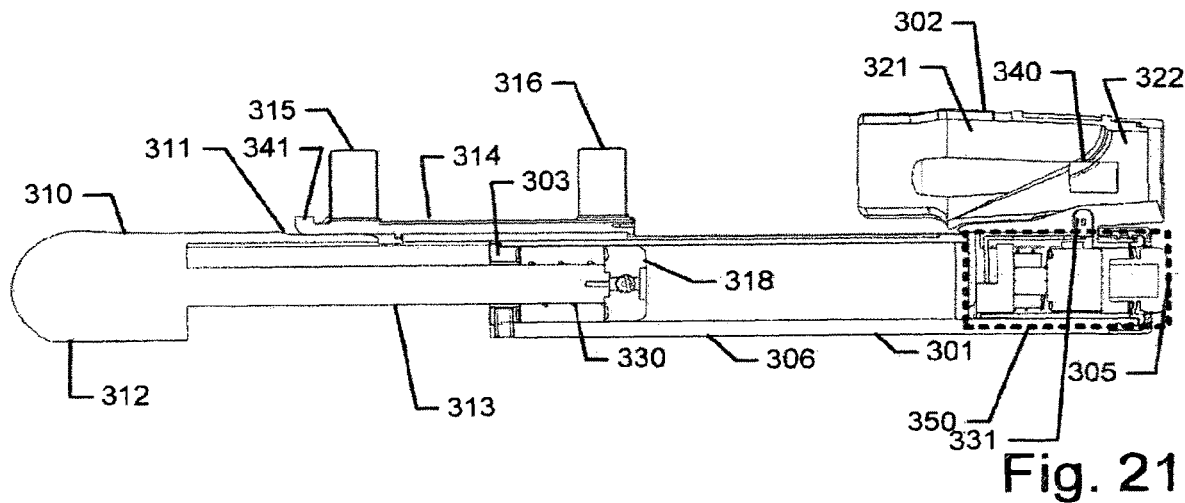
Figure 22:
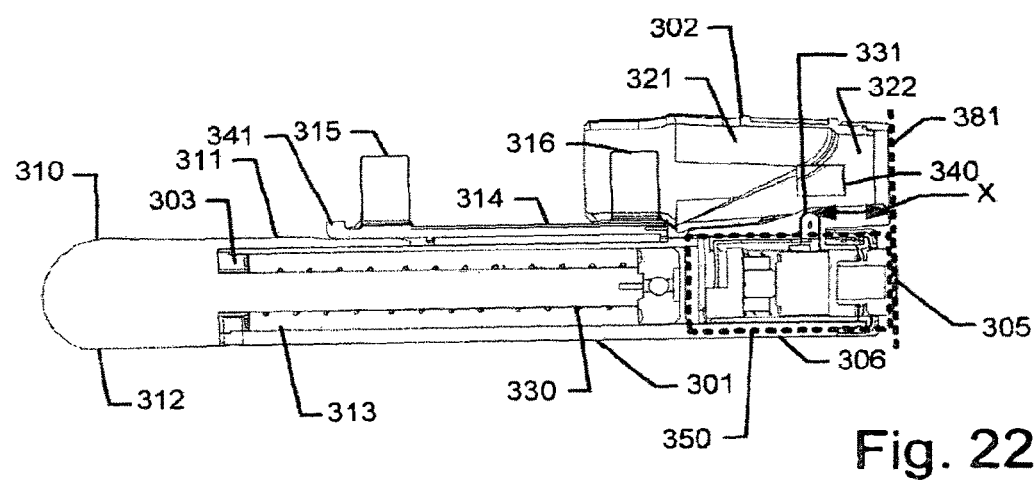
Figure 23:
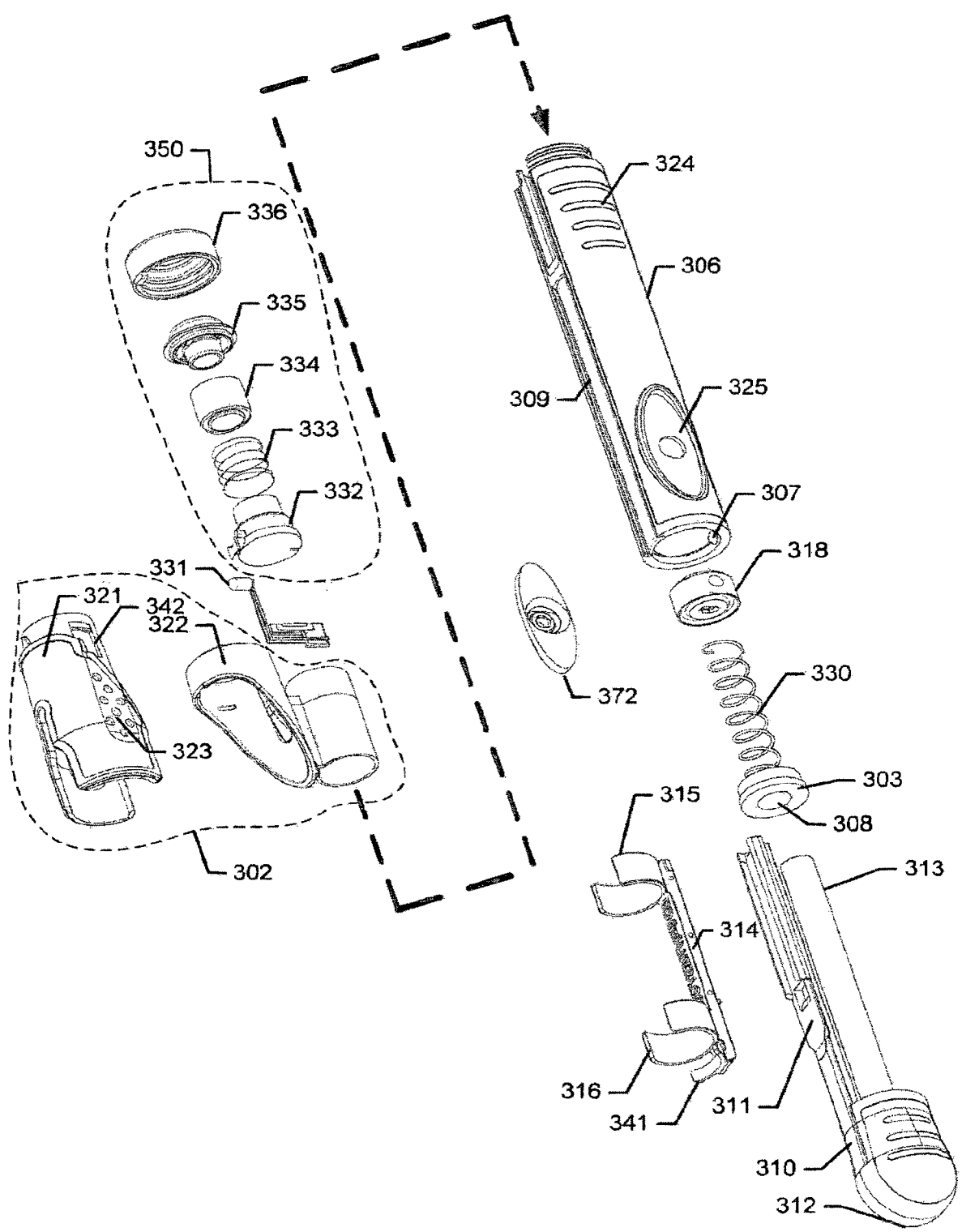

FIGS. 18-23 show different views of an injection device 300 for injecting a hypodermic syringe along an injection direction defining an injection axis 380 according to an embodiment of the present invention. In the following, reference will be made to FIGS. 18-23. The injection device 300 comprises a housing 301 and a movable element 310 movable arranged relative to said housing 301 between a retracted position and an injection position. FIG. 18 shows a perspective view, FIG. 19 shows a side view with the movable element in the injection position, FIG. 20 shows a side view with the movable element in the retracted position, FIG. 21 shows a central cross-section with the movable element in the retracted position, FIG. 22 shows a central cross-section with the movable element in the injection position, and FIG. 23 shows an exploded view. The movable element 310 comprises a syringe holder 314 for holding a syringe. The syringe holder (314) comprises a first set of gripping arms 315 and a second set of gripping arms 316. The housing 301 comprises an elongated main body, which in this embodiment is a first tubular element 306.

The movable element 310 comprises a first portion 313 arranged to slide inside the first tubular element 306 of the housing 301, a second portion 311 arranged to slide at a first outer surface of the housing 301, and a connection portion 312 connecting the first portion 313 with the second portion 311, wherein the movable element 310 extends out of an upper opening 307 of the first tubular element 306.

This allows a user to more freely grip and handle the injection device 300 e.g. a gripping zone 323 may be formed in the lower third part of the injection device 300 providing better control to the user.

The injection device 300 is configured so that when the movable element 310 is in the retracted position (see FIGS. 20 and 21), the first portion 313 is extending out of the first tubular element 306 through the upper opening 307 of the first tubular element 306, and when the movable element 310 is in the injection position (see FIGS. 19 and 20), the first portion 313 is entirely positioned inside the first tubular element 306 and the second portion 311 and the connection portion 312 are positioned entirely outside the housing 301. The first outer surface of the housing 301 comprises a groove 309 extending along the injection axis 380. The second portion 311 of the movable element 310 engages with the groove 309.

The connection portion 312 comprises a handle 326 allowing a user, when the movable element 310 is in the injection position, to grip the movable element 310 and retracts the movable element 310 back into the retracted position.

The housing 301 further comprises a second tubular element 303 inserted into the top of the first tubular element 306. The movable element 310 extends out of the second tubular element 303. The movable element 310 is configured so that a part of the first portion 313 slides along an inner surface of the second tubular element 303 element thereby providing additional mechanical stability i.e. the first portion 313 comprises a cylindrical element that approximately fits the inner diameter 308 of the second tubular element 303.

The injection device 300 further comprises a spring 330 connecting the movable element 310 with the housing 301. In this embodiment the spring 330 is a compression spring i.e. a spring that when compressed stores mechanical energy. The first portion 313 of the movable element 310 further comprises a disc 318 having a surface interacting with the spring 330. The disc 318 has a shape matching the shape of the inner surface of said first tubular element 306 thereby providing further mechanical stability.

The spring 330 surrounds a part of the first portion 313 of the movable element 310 and has a first end that abuts a first upper surface of the disc 318 and a second end that abuts a lower surface of the second tubular element 303. Thus, when the movable element 310 is in the retracted position, the spring is compressed and thereby stores mechanical energy that can be used to move the movable element 310 from the retracted position to the injection position whereby a hypodermic syringe attached to the hypodermic syringe holder 314 may be injected.

The housing 301 comprises a planar contact surface 305 for being positioned at the skin, wherein the planar contact surface 305 is positioned in a plane 381 (see FIG. 19) being angled with an angle 382 of 90 degrees relative to said injection axis 380.

An angle of 90 degrees may be suitable for making intramuscular injections.

The housing 301 further comprises a needle shield 302 attached to the first tubular element 306. The needle shield 302 is in this embodiment a tubular needle shield. The needle shield 302 forms part of a gripping zone 390 (as shown on FIG. 20). The gripping zone 390 comprises a first set of gripping elements 324 arranged on the first tubular element 306, and a second set of gripping elements 323 arranged on the needle shield 302. The first and the second set of gripping elements 324 323 are suitable for receiving one or more fingers. The gripping zone 390 is positioned in the lower third part of the housing 301. The gripping zone 390 is configured to allow a user to safely hold the injection device 300 at any position of said gripping zone while a hypodermic syringe is being injected.

The movable element 310 is arranged in a manner relative to the housing 301 so that at least 65% of the outer circumference of any cross-section of the housing 301 being perpendicular to the injection axis 380 does not interact with the movable element 310 at any possible position of the movable element 310. Thus a user may hold the injection device 300 at the skin with a single handed grip at the gripping zone without risking interfering with the movement of the movable element 310. The needle shield has a minimum height 383. The minimum height is measured as the minimum width of the needle shield 302 along the injection axis 380.

The injection device 300 comprises a release mechanism 325 for releasing the spring 330, whereby the movable element 310 is moved from the retracted position to the injection position. The release mechanism 325 may be a release mechanism as explained in relation to the seventh aspect of the invention. i.e. a release mechanism that is partly inserted into an opening (317) of the movable element 310, wherein the release mechanism is movably arranged between gripping position and a release position along a release mechanism axis.

The injection device 300 further comprises a locking mechanism 372. The locking mechanism 372 may be a locking mechanism as explained in relation to the seventh aspect of the invention.

The injection device 300 further comprise a light source 331 wherein the light source 331 is arranged so that when it is activated and the movable element 310 is in the injection position, the peak intensity of the resulting light beam is positioned at or below the needle hub connecting an hypodermic needle with an hypodermic syringe attached to the hypodermic syringe holder 314 e.g. see FIG. 25. This allows a user to detect blood present in the needle hub or in the hypodermic needle before it is withdrawn into the hypodermic syringe.

The light source may be positioned inside said needle shield with a distance X to the planar contact surface 381 of the housing (see FIG. 22). The needle shield 302 comprises an inspection window 340 arranged at a position allowing a user to inspect a needle hub or hypodermic needle, of a hypodermic syringe attached to the hypodermic syringe holder 314. The inspection window 340 is bordered by a non transparent part of the needle shield 302.

Consequently, the injection of the hypodermic syringe/needle may be hidden from the user, while the user still may clearly inspect whether a blood vessel has been hit.

The needle shield 302 is an assembly assembled from a first part 322 attached to the first tubular element 306, and a second part 321 inserted into the first part 322.

In this embodiment, the first part 322 of the needle shield 302 is made of a transparent material and the second part 321 is partly made of a non transparent material. The second part 321 comprises a through hole 342 partly positioned in the portion of the second part 321 being inserted into the first part 322. It is this through hole that together with the first part 322 forms the inspection window 340.

The housing 301 further comprises a pressure sensor 350 operatively connected to the light source 331. The pressure sensor 350 is configured to detect the contact pressure between the housing 301 and the skin, and the injection device is configured to control the light source 331 to signal to the user that the injection device is ready for injecting a hypodermic syringe. In this embodiment the light source signals to the user that the injection device is ready by being turned on.

In this embodiment, as depicted in FIG. 23, the pressure sensor 350 comprises a closing lid 336 to keep the pressure sensor 350 in place, a button 335 movably arranged between a first position and a second position, a pressure sensor spring 333, a power source 334, and an electric switch (332) configured to make or break a first electric circuit between said light source 331 and said power source (334), wherein said electric switch 332 is configured to make said first electric circuit when said button 335 is at said second position; said pressure sensor spring 333 is arranged to keep the button away from said second position until a contact pressure larger than said first threshold is acting on said button 335. Thus, in this embodiment, the injection device 300 is mechanically configured to control the light source 331 to signal to the user that the injection device is ready for injecting a hypodermic syringe after the pressure sensor has detected contact between the injection device and the skin of the user.

Consequently, the user may be prevented from applying too much contact pressure whereby the risk of bone injections may be lowered.

Figure 24:
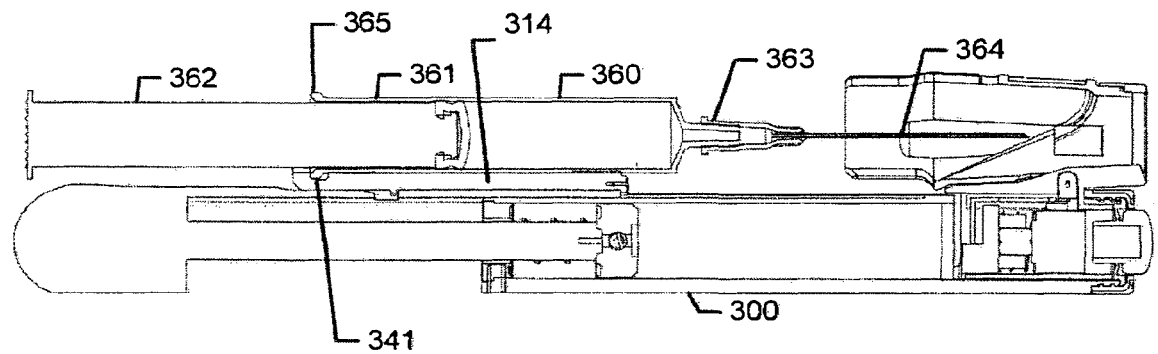
FIG. 24 shows a side view of an injection device comprising a hypodermic syringe with the movable element in the retracted position according to an embodiment of the present invention.
Figure 25:
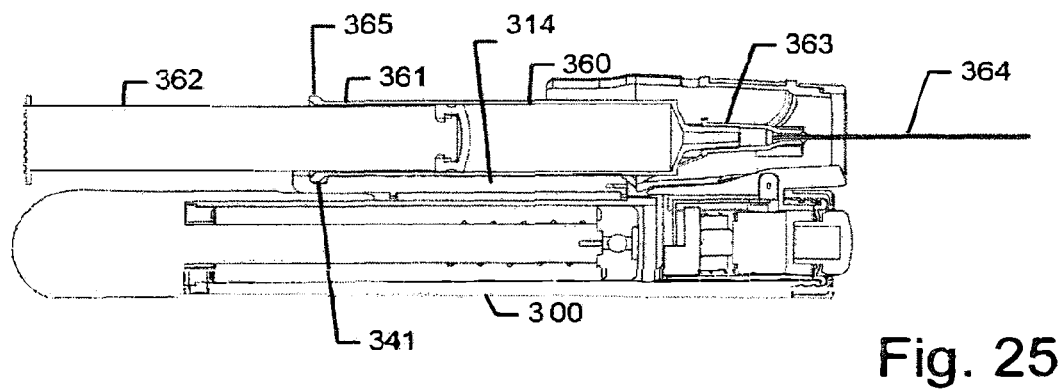
FIG. 25 shows a side view of an injection device comprising a hypodermic syringe with the movable element in the injection position according to an embodiment of the present invention.

FIGS. 24 and 25 show an injection device 300 comprising a hypodermic syringe 361 having a barrel 360 and a plunger 362 according to an embodiment of the invention. FIG. 24 shows the injection device 300 with the movable element in the retracted position and FIG. 25 shows the injection device 200 with the movable element in the injection position. The injection device 200 is identical to the injection device shown in FIGS. 18 to 23. The hypodermic syringe 361 is connected to a hypodermic needle 364 through a needle hub 363. The syringe holder 314 further comprises a groove 341 for gripping the collar 365 of the hypodermic syringe 361. The groove 341 is configured to prevent the hypodermic syringe 361 to move relative to the hypodermic syringe holder 314 along the injection axis.

Figure 26:
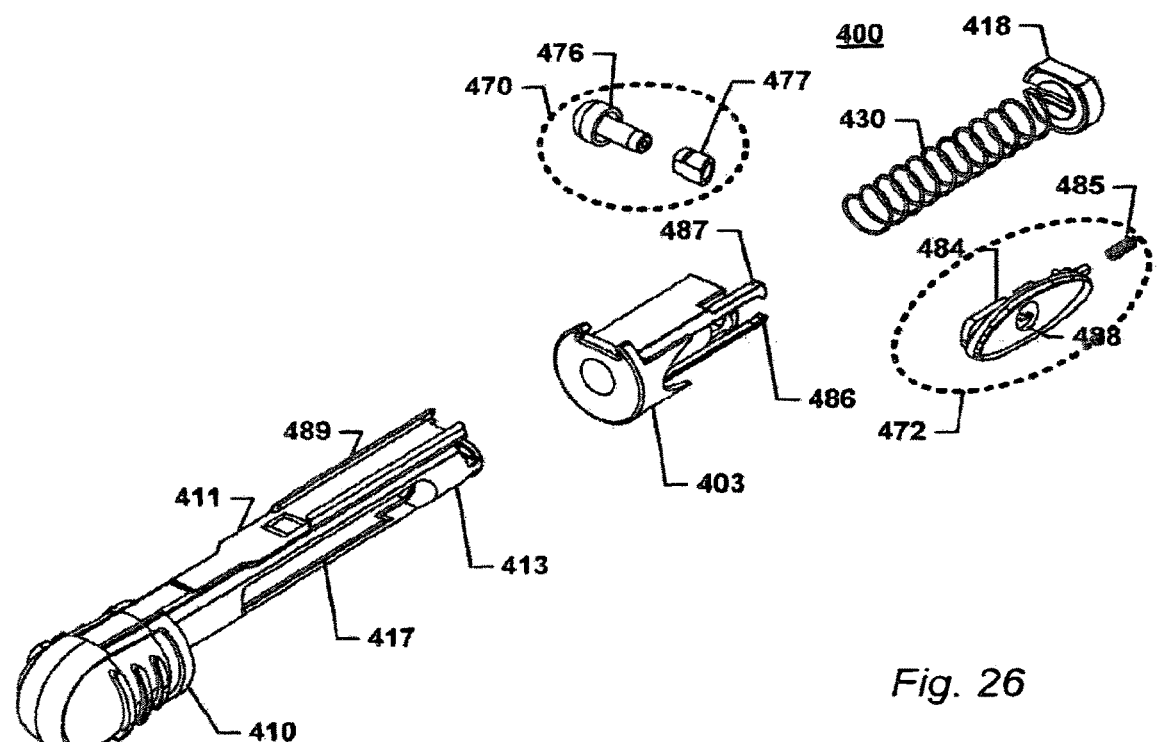
Figure 27A:
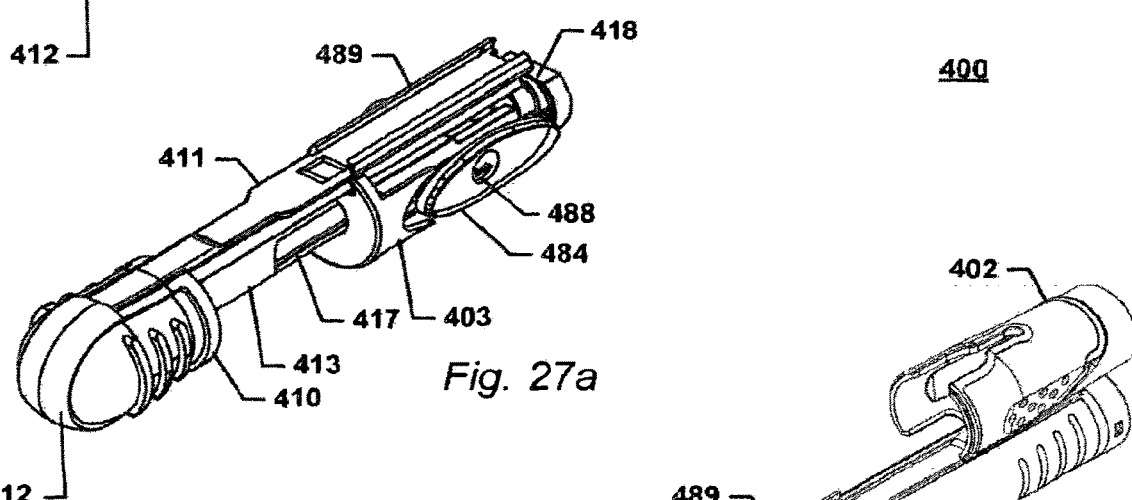
Figure 27B:
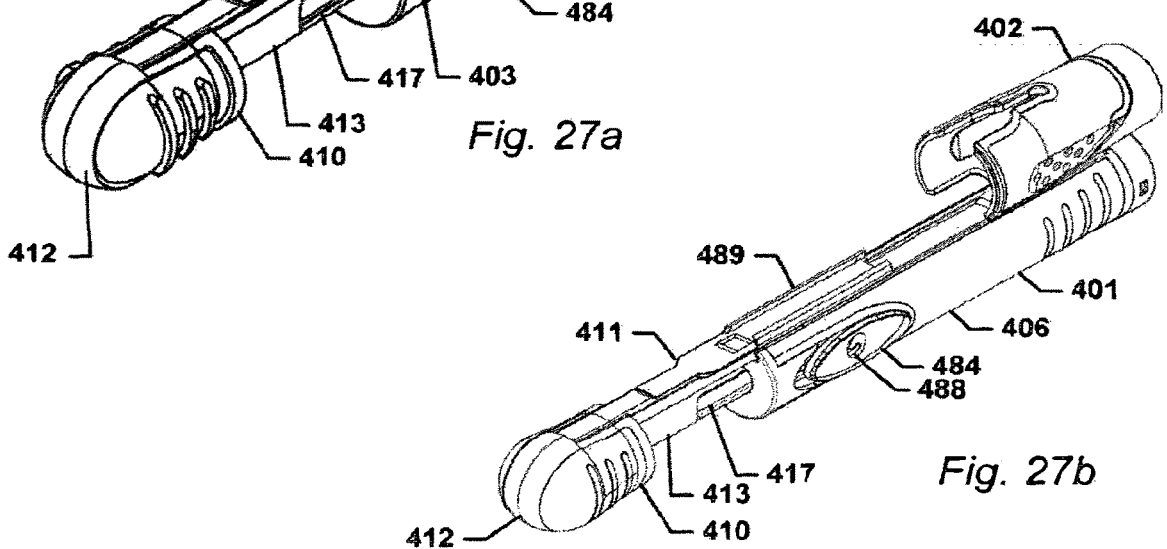
Figure 31A:
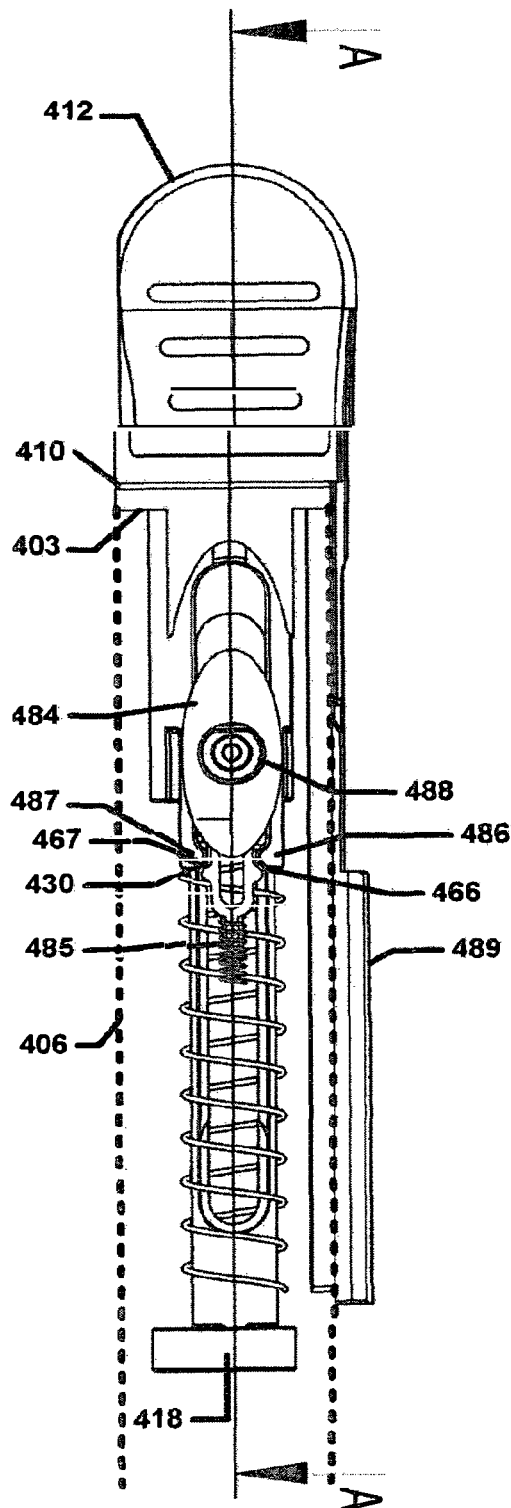
FIG. 31a shows a side view.
Figure 31B:
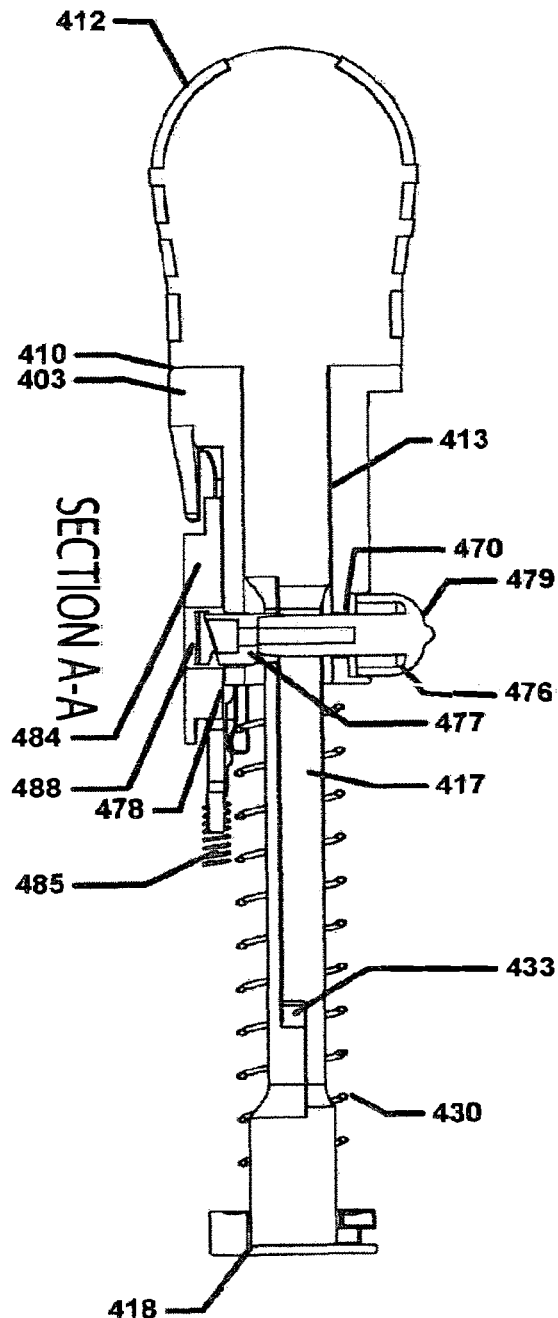
FIG. 31b shows a cross-sectional view.
Figure 32A:
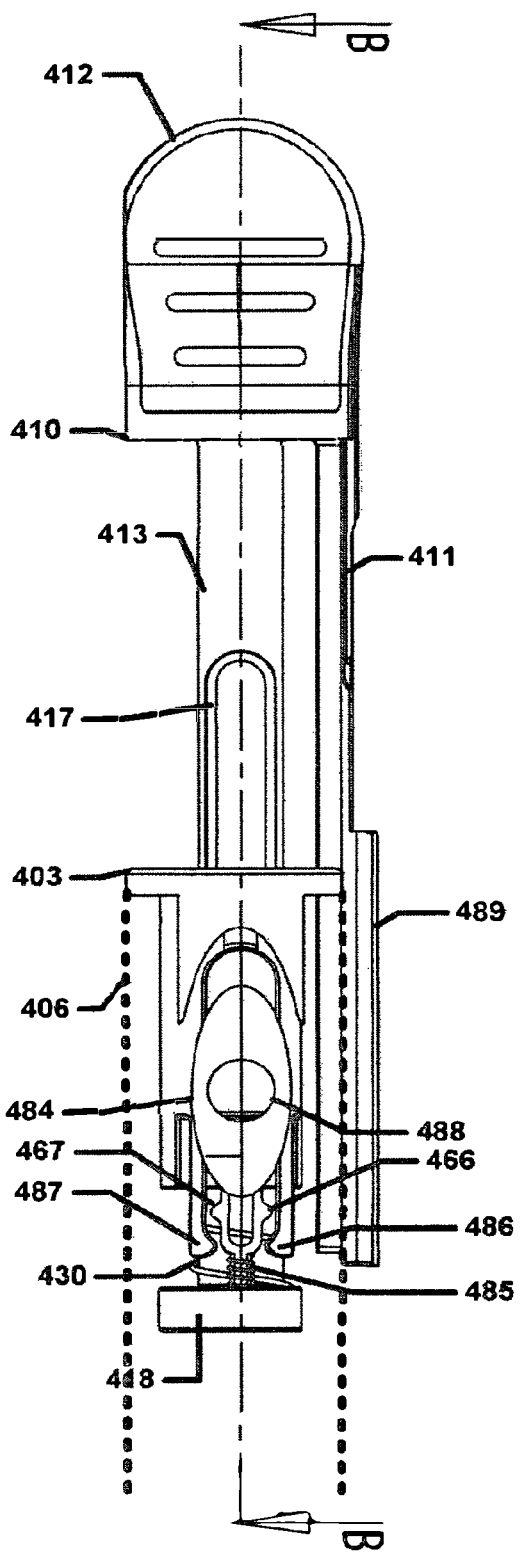
FIG. 32a shows a side view.
Figure 32B:
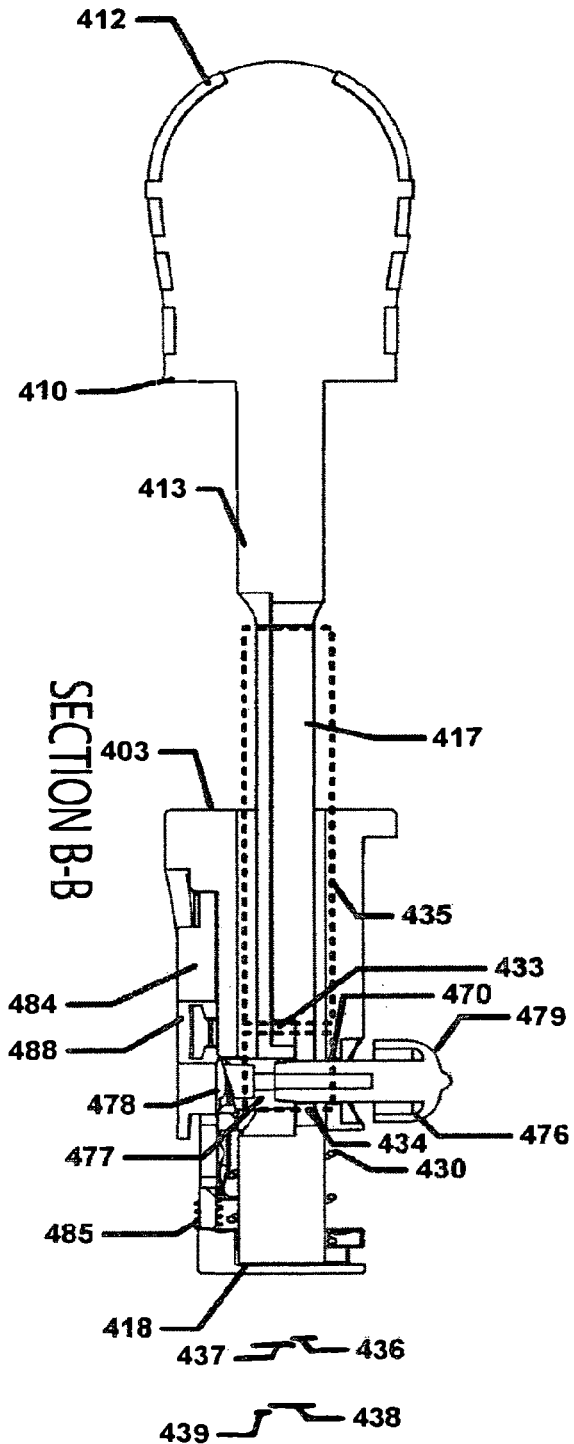

FIGS. 26-32b show different views of parts of an injection device 400 according to an embodiment of the present invention. FIG. 26 shows an exploded view, FIG. 27a-b show a perspective view, FIG. 28a shows a side view, FIG. 28b shows a cross-sectional view along the line B in FIG. 28a, FIG. 29a shows a side view, FIG. 29b shows a cross-sectional view along the line B in FIG. 29a, FIG. 30a shows a side view, FIG. 30b shows a cross-sectional view along the line B in FIG. 30a, FIG. 31a shows a side view, FIG. 31b shows a cross-sectional view along the line A in FIG. 31a, FIG. 32a shows a side view and FIG. 32b shows a cross-sectional view along the line B in FIG. 32a. In the following reference will be made to FIGS. 26-32b.

The figures illustrate the functioning of a release mechanism 470 and a locking mechanism 472 according to an embodiment of the present invention. Shown is an injection device 400 comprising a housing 401 and a movable element 410. The housing 401 comprises a first tubular element 406, a needle shield 402, and a second tubular element 403 inserted into the upper opening of the first tubular element 406. The movable element 410 is movably arranged relative to the housing 401 between a retracted position and an injection position. The movable element comprises a first portion 413 arranged to slide inside said first tubular element 406, a second portion 411 arranged to slide at a first outer surface of said housing 401, and a connection portion 412 connecting said first portion 413 with said second portion 411. The second portion 411 comprises two sections 489 for receiving a hypodermic syringe holder. The hypodermic syringe holder is not shown in FIGS. 26-32, but it should be understood that it may be of a type similar to the hypodermic syringe holders shown in FIGS. 1-25. The first tubular element 406 is only fully shown in FIG. 27b, in FIGS. 26 and 27a it has been completely removed, and in FIG. 28a-32b is has been shown schematically. This has been done to better illustrate the functioning of the internal elements of the injection device 400. It should be understood that the release mechanism and/or locking mechanism shown may be implemented in any one of the three injection devices shown in FIGS. 1-27.

The injection device further comprises a spring 430 connecting the movable element 410 with the housing 401. The spring 430, when released, is configured to move the movable element 410 from the retracted position (shown in FIGS. 28-29) to the injection position (shown in FIG. 31), along an injection axis 480 (shown in FIG. 28a) whereby a hypodermic syringe may be injected. The first portion 413 of the movable element 410 comprises a disc 418 having an outer surface interacting with the spring 430.

The injection device 400 further comprises a release mechanism 470 configured to allow a user to release the spring 430. The release mechanism 470 is movably arranged between a gripping position and a release position along a release mechanism axis 431 (shown in FIG. 28b). The release mechanism 470 is shown in the gripping position in FIGS. 28b, 29b, and 32b, and in the release position in FIGS. 30b and 31b. The release mechanism 470 is partly inserted into an elongated through hole 417 in the movable element. When the movable element 410 is in the retracted position, the release mechanism 470 is arranged to release the spring 430 by being moved from the gripping position to the release position, whereby the movable element is moved to the injection position. Consequently, by providing a release mechanism that releases the spring by being moved along an axis, a release mechanism that is easy and safe to operate is provided.

The release mechanism 470 is extending through a first side opening in the housing (not shown as the main part of the housing is only schematically illustrated) and comprises a contact surface 479 that faces away from the housing 401, wherein the release mechanism 470 is configured to be moved from the gripping position to the release position in response to a user pushing on the contact surface 479. The release mechanism 470 is an assembly of a first element 476 and a second element 477. The first element 476 constitutes a first portion of the release mechanism 470 and the second element 477 constitutes a second portion of the release mechanism 470. When the release mechanism 470 is in the gripping position and the movable element 410 is in the retracted position, the second element 477 abuts the movable element 410 inside the elongated through hole 417 at an internal contact surface 433 and the spring 430 pushes the internal contact surface 433 towards the second portion 477 (the internal contact surface 433 can be seen in FIGS. 30b, 31b and 32b). The release mechanism 470 is configured so that, when it is moved from the gripping position to the release position, the second portion 477 no longer abuts the internal contact surface 433, whereby the spring 430 is released and the movable element 410 moves to the injection position.

Figure 29A:
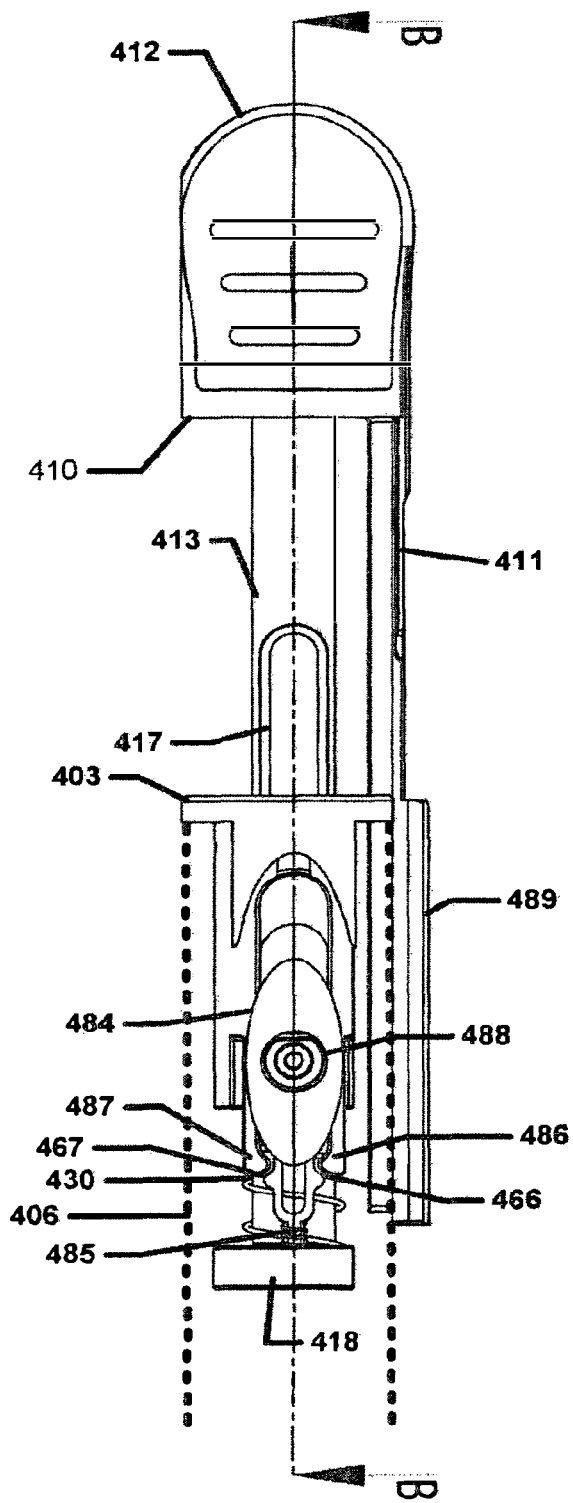
FIG. 29a shows a side view.
Figure 29B:
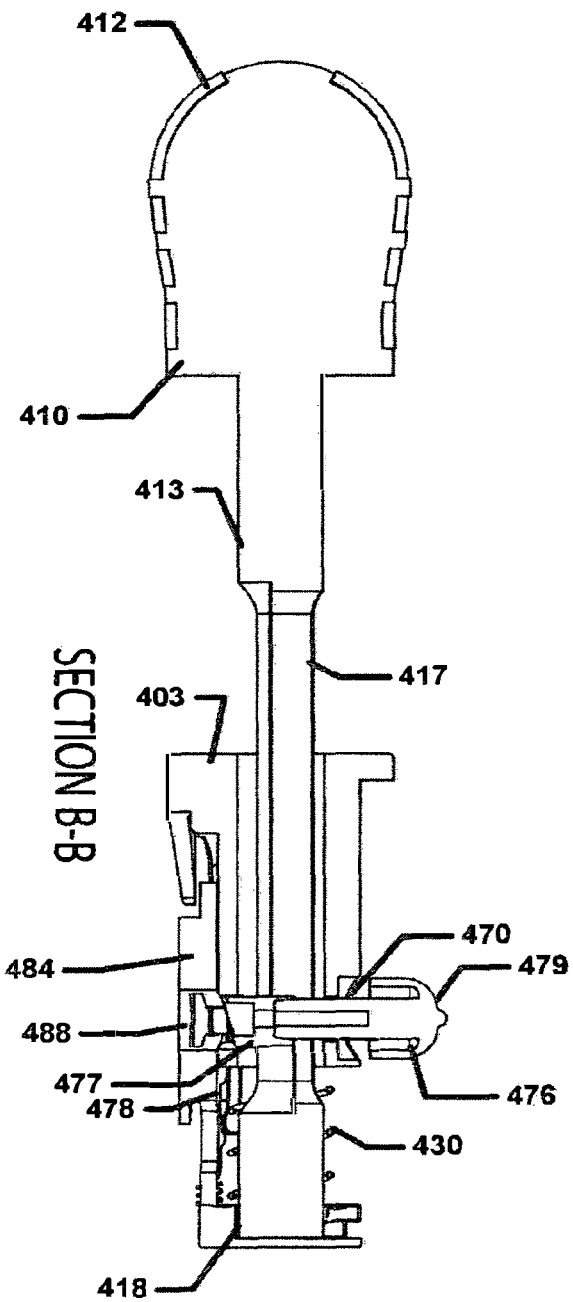
FIG. 29b shows a cross-sectional view.

The elongated opening 417 comprises along the injection axis 480 a first zone 434 at a lower end of the elongated opening 417 and a second zone 435 positioned next to the first zone 434, the release mechanism 470 being positioned in the first zone 434 when the movable element 410 is in the retracted position and in the second zone 435 when the movable element 410 is moving towards the injection position. The elongated opening 417, at the first zone 434, along the release mechanism axis 431, has a part with a first width w1 and a part with a second width w2, said first width w1 being larger than the width of the first element 476 of the release mechanism 470 but smaller than the width of the second element 477 of the release mechanism 470, where the second width w2 is larger than the width of the second element 477 of the release mechanism 470. The elongated through hole, at the second zone 435, along the release mechanism axis 431, has a part with a third width w3 and a part with a fourth width w4, the third width w3 being larger than the width of the first element 476 of the release mechanism 470 but smaller than the width of the second element 477 of the release mechanism 470, the fourth width w4 being larger than the width of the second element 477 of the release mechanism 470. The second width w2 extends along a longer part of the release mechanism axis 431 than the fourth width w4, and wherein the internal contact surface 433 constitutes a part of the interface between the first zone 434 and the second zone 435. In FIG. 32b the line 436 shows the extent of the first width w1, the line 437 shows the extent of the second width w2, the line 438 shows the extent of the third width w3, and the line 439 shows the extent of the fourth width w4 along the release mechanism axis 431. It should be noted that all widths are measured along an axis being perpendicular to both the injection axis 480 and the release mechanism axis 431. Thus, when the release mechanism 470 is positioned in the gripping position as shown in FIG. 29b, the second element 477 is aligned with the part of the second zone 435 having the third width w3 and as the third width w3 is smaller than the width of the second element of the release mechanism 477, the release mechanism 470 prevents the spring 430 from moving the movable element 410 along the injection axis 480 towards the injection position. When the release mechanism 470 is moved to the release position, as shown in FIG. 30b, the second element 477 is aligned with the part of the second zone 435 having the fourth width w4 and as the fourth width w4 is larger than the width of the second element of the release mechanism 477, the release mechanism 470 now allows the spring 430 to move the movable element 410 along the injection axis 480 towards the injection position. Thus, the second part 477 of the release mechanism 470 is arranged in the part of the second zone 435 having the fourth width w4, when the movable element 410 is moving toward the injection position.

The injection device 400 further comprises a locking mechanism 472. The locking mechanism 472 is movably arranged between a locked position and an un-locked position along a locking mechanism axis 432 (shown in FIG. 28a) wherein the locking mechanism 472 is configured to, when it is positioned in the locked position, prevent the release mechanism 470 from being moved from the gripping position to the release position. Thus, a safer injection device is provided as unintentional release of the spring may be avoided.

The locking mechanism 472 is shown in the locked position in FIGS. 28a-b, and 32a-b, and in the un-locked position in FIGS. 29a-b, 30a-b, and 31a-b.

The locking mechanism 472 is slidably arranged in a second side opening of the housing, the second side opening being opposite to the first side opening (the side opening the release mechanism 470 is extending through), the locking mechanism 472 comprises a blocking surface 478 facing the housing 401. The blocking surface 478 is aligned with the release mechanism axis 431 when the locking mechanism 472 is in the locked position and unaligned with said release mechanism axis 431 when the locking mechanism 472 is in the un-locked position. Thus, the blocking surface 478 prevents the release mechanism 470 from moving along the release mechanism axis 431 toward the release position, when the locking mechanism 472 is positioned in the locked position. As can be seen in FIGS. 30b and 31b the release mechanism 470 extends past the blocking surface 478, when the release mechanism 470 is positioned in the release position. In this embodiment, the locking mechanism 472 comprise a through hole 488 arranged next to the blocking surface 478, and the release mechanism 470 is arranged so that it in the release position it is extending through both the elongated through hole 417 of the movable element 410 and further extends into the through hole 488 of the locking mechanism 472.

Figure 28A:
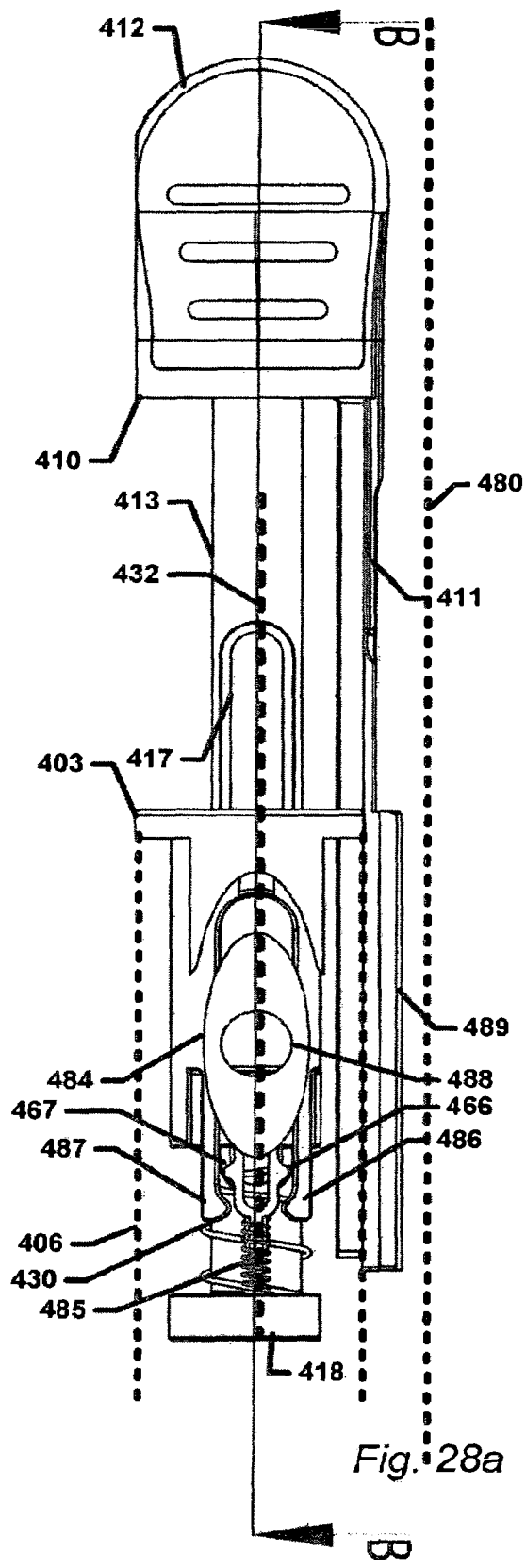
FIG. 28a shows a side view.
Figure 28B:
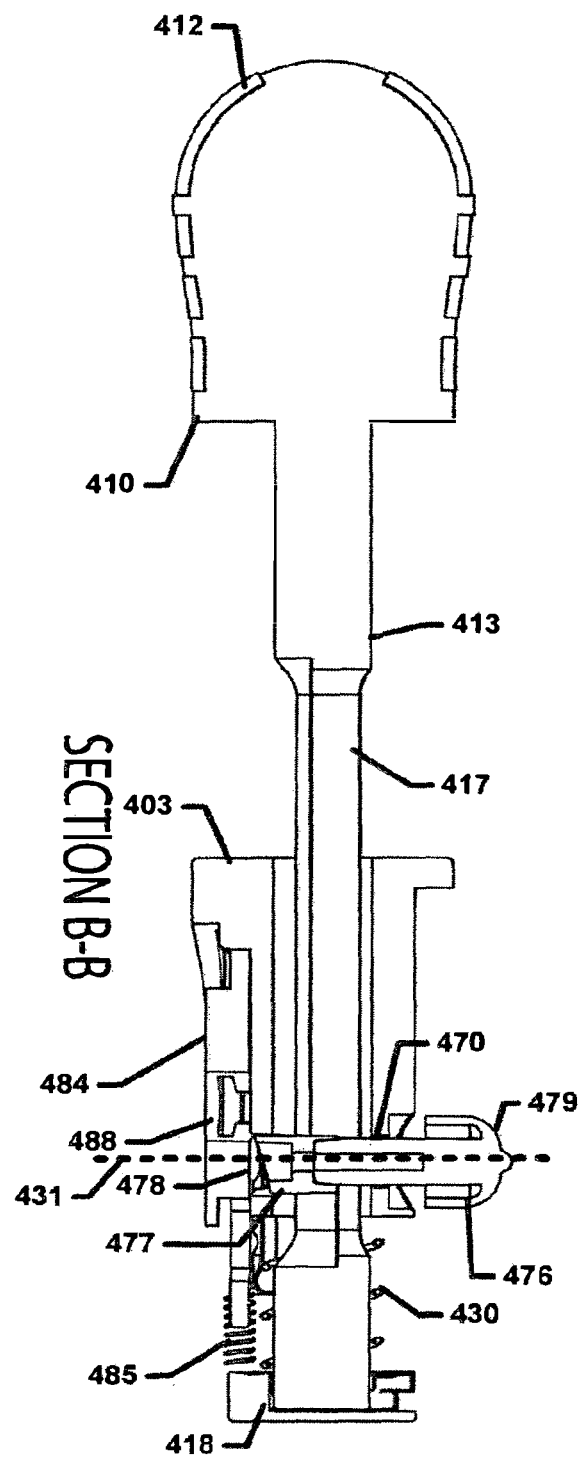
FIG. 28b shows a cross-sectional view.

The locking mechanism 472 at a first end facing the disc 418 of the movable element 410 comprises a spring 485. The movable element 410, via the disc 418, is configured to, when being manually moved from the injection position to the retracted position, push on the locking mechanism spring 485 thereby causing the locking mechanism 472 to move from the un-locked position to the locked position. Consequently, an unintentional release of the spring 430 after an injection has been made may be prevented. This is especially important, when the injection device 400 is used by medical professionals as the hypodermic syringe after use may be contaminated with infectious diseases. This is illustrated in FIGS. 31-32. In FIG. 31b the movable element 410 is in the injection position, and the locking mechanism 472 is in the un-locked position. In FIG. 32b the movable element 410 is manually moved back into the retracted position, whereby the disc 418 pushes on the locking mechanism spring 485, and the locking mechanism is moved to the locked position. It can be seen that the movable element in FIG. 32b is retracted a distance past the retracted position, as the second element 477 of the release mechanism 470 is not abutting the internal contact surface 433. Thus, in FIG. 32b a user is manually holding movable element 410. When the movable element is released, it will by the force of the spring 430 be moved to the retracted position as shown in FIG. 28b.

By providing the locking mechanism with a spring, a more compact injection device may be provided as the space requirements of the locking mechanism may be reduced. If the locking mechanism does not comprises a spring, the movable elements needs to be able to move a significant distance past said retracted position, to be able to push the locking mechanism from said un-locked position to said locked position, and further allow said locking mechanism, when the movable element is in the retracted position, to move from said locked position to said un-locked position without interfering with the disc 418 of the movable element 410.

The locking mechanism 472 is arranged so that the locking mechanism spring 485 is partly compressed, when the movable element 410 is in the retracted position and the locking mechanism 472 is in the un-locked position, and provides a first force (F1) along the locking mechanism axis 432 in a direction towards the locked position. The housing 401 comprises two gripping members 486 487 configured to prevent the locking mechanism 472 from moving from the un-locked position to the locked position, unless a second force (F2) along the locking mechanism axis 432 in a direction towards the locked position is acting on the locking mechanism 472, the second force (F2) being higher than the first force (F1), whereby the locking mechanism can stay at the un-locked position without assistance from the user. In this embodiment the two gripping members 486 487 forms part of the second tubular element 403. The second tubular element 403 interacts with a release mechanism 484 located in the locking mechanism 472. The two gripping members 486 487 interact with two protrusions 466 467 of the locking mechanism 472. The two protrusions 466 467 causes the two gripping members 486 487 to bend slightly outwards when a force above F2 along the locking mechanism axis 432 in a direction towards the locked position is acting on the locking mechanism 472, whereby the two protrusions 466 467 may move past the two gripping members 486 487.

The release mechanism 470 is further arranged to move from the release position to the gripping position, when the movable element 410 is moved from the injection position to the retracted position. In this embodiment, this is achieved via the movement of the locking mechanism 472 i.e. when the locking mechanism 472 is moving from the un-locked position to the locked position the lower edge of the through hole 488 pushes on a sloping end surface of the second element 477 so that a force induced by the locking mechanism 472 is acting on the release mechanism 470 along the release mechanism axis 431, moving the release mechanism 470 from the release position to the gripping position. This allows the injection device in an easy manner to be re-used for performing further injection, as there is no need for a complicated re-setting procedure.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

What is claimed is:

1. An injection device for injecting a hypodermic syringe along an injection direction defining an injection axis, said injecting device comprising:
   a housing for being positioned at a user's skin, wherein said housing comprises:
      an elongated main body having an upper opening,
      a needle shield attached to said elongated main body, said needle shield being a tubular element and comprising a first opening configured to face said skin when the injection device is positioned at said skin,
      a planar contact surface for being positioned at said skin,
      a gripping zone in a lower third part of said housing, said needle shield forming part of said gripping zone, said gripping zone being configured to allow the user to safely hold said injection device at any position of said gripping zone while the hypodermic syringe is being injected by said injection device; and
   a movable element movably arranged relative to said housing between a retracted position and an injection position, wherein said movable element comprises a hypodermic syringe holder for holding the hypodermic syringe outside of the housing, said movable element comprising a first portion arranged to slide inside said elongated main body of said housing, a second portion arranged to slide at a first outer surface of said housing, and a connection portion connecting said first portion with said second portion, wherein said movable element extends out of said upper opening of elongated main body, wherein said needle shield is arranged so that a tip of a hypodermic needle of the hypodermic syringe attached to said hypodermic syringe holder is positioned completely inside the needle shield when the movable element is in the retracted position and so that the tip of the hypodermic needle protrudes from the needle shield when the movable element is in the injection position.

2. The injection device according to claim 1, wherein said needle shield has a minimum height of at least 1 cm.

3. The injection device according to claim 2, wherein said gripping zone comprises a first concave portion for receiving one or more fingers of the user.

4. The injection device according to claim 3, wherein said gripping zone further comprises a second concave portion for receiving one or more fingers of the user.

5. The injection device according to claim 4, wherein said first concave portion and/or said second concave portion comprises a plurality of protruding elements for providing a high frictional contact with the one or more fingers of the user.

6. The injection device according to claim 1, wherein said planar contact surface is positioned in a plane being angled with an angle below 75 degrees relative to said injection axis.

7. The injection device according to claim 1, wherein said needle shield comprises an inspection window arranged at a position allowing the user to inspect the hypodermic needle or needle hub.

8. The injection device according to claim 1, wherein said movable element can be retracted from the injection position to the retracted position.

9. The injection device according to claim 1, wherein said movable element is arranged in a manner relative to said housing so that at least 65% of an outer circumference of any cross-section of said housing being perpendicular to said injection axis does not interact with said movable element at any possible position of said movable element.

10. The injection device according to claim 1, wherein a part of said gripping zone comprises a material for establishing a high frictional contact with a hand of the user.

11. The injection device according to claim 1, wherein said needle shield is an assembly assembled from a first part attached to said elongated main body, and a second part inserted into said first part.

12. The injection device according to claim 1, wherein said needle shield and said elongated main body is integrally molded.

13. The injection device according to claim 1, wherein said injection device is an intramuscular injection device for intramuscularly injecting the hypodermic syringe.

14. The injection device according to claim 1, wherein said injection device is a subcutaneous injection device for subcutaneously injecting the hypodermic syringe along a central axis of said injection device.

15. A method of injecting a hypodermic syringe, comprising:

obtaining the injection device as specified in claim 1;

arranging the hypodermic syringe having a hypodermic needle attached in the hypodermic syringe holder of the injection device;

positioning the injection device at the skin of a recipient;

while holding the injecting device at the gripping zone positioned in the lower third part of said injection device's housing, pushing a release mechanism on the injection device, whereby the movable element moves to said injection position and the hypodermic syringe is injected.

* * * * *